United States Patent [19]

Carson et al.

[11] Patent Number: 5,298,652
[45] Date of Patent: Mar. 29, 1994

[54] N-SUBSTITUTED GLYCINES, INHIBITORS OF PHOSPHOLIPASE $A_2$

[75] Inventors: Mathew Carson, Nutley; Ru-Jen L. Han, Princeton Junction; Ronald A. LeMahieu, N. Caldwell; Vincent S. Madison, Mountain Lakes, all of N.J.

[73] Assignee: Hoffmann-La Roche Inc., Nutley, N.J.

[21] Appl. No.: 987,229

[22] Filed: Dec. 8, 1992

[51] Int. Cl.$^5$ .......................................... C07C 229/34
[52] U.S. Cl. .................... 562/444; 562/450; 554/61; 554/105; 560/39; 560/41; 560/29; 560/34
[58] Field of Search ................. 562/444, 450; 560/39, 560/41; 514/558, 559, 563, 566, 567, 512

[56] References Cited
PUBLICATIONS

Chemical Abstract 82(25): 171450u; 1974.
J. Med. Chem., 9, 197(1966).
CA:111, 115135.
CA:99, 70177.
CA:95, 61756.
CA:91, 192767.
CA:70, 87228.

*Primary Examiner*—José G. Dees
*Assistant Examiner*—Samuel Barts
*Attorney, Agent, or Firm*—George M. Gould; William C. Isgro

[57] ABSTRACT

Compounds of the formula

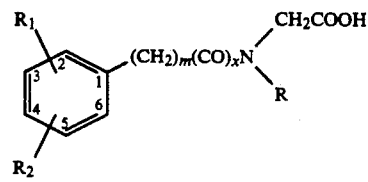

R is hydrogen or $-CH_2COOH$;
m is 0-2,
x is 1-2, with the provision that when x is 2, m is always 0;
$R_1$ is $CH_3(CH_2)_nO-$, $CH_3(CH_2)_nCONH-$, $CH_3(CH_2)_nNHCONH-$, $CH_3(CH_2)_nNHCOO-$, $HOOC(CH_2)_pO-$ or $R_3(CH_2)_qO-$;
$R_2$ is hydrogen, carboxy, hydroxy, nitro, amino, $CH_3(CH_2)_nO-$, $CH_3(CH_2)_nCONH-$, $CH_3(CH_2)_nNHCONH-$, $CH_3(CH_2)_nNHCOO-$, $HOOC(CH_2)_pO-$, $R_3(CH_2)_qO-$ or $R_4[O(CH_2)_2]_rO-$,
wherein n is 0-17, p is 1-10, q is 1-12, r is 1-6,
$R_3$ is 1- or 2- naphthyloxy, 2,3- or 3,4-dihydroxyphenyl, phenyl, phenoxy or substituted phenyl or phenoxy, wherein the substituent is selected from the group consisting of lower alkyl, lower alkoxy, hydroxy, nitro, amino, halo, carboxy or phenyl, and
$R_4$ is lower alkyl;
and pharmaceutically acceptable salts with bases, are described.

19 Claims, No Drawings

N-SUBSTITUTED GLYCINES, INHIBITORS OF PHOSPHOLIPASE $A_2$

BRIEF SUMMARY OF THE INVENTION

The invention relates to compounds of the formula

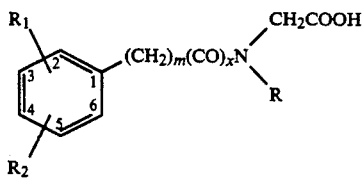

R is hydrogen or —$CH_2COOH$;
m is 0–2,
x is 1–2, with the provision that when x is 2, m is always 0;
$R_1$ is $CH_3(CH_2)_nO$—, $CH_3(CH_2)_nCONH$—, $CH_3(CH_2)_nNHCONH$—, $CH_3(CH_2)_nNHCOO$—, $HOOC(CH_2)_pO$— or $R_3(CH_2)_qO$—;
$R_2$ is hydrogen, carboxy, hydroxy, nitro, amino, $CH_3(CH_2)_nO$—, $CH_3(CH_2)_nCONH$—, $CH_3(CH_2)_nNHCONH$—, $CH_3(CH_2)_nNHCOO$—, $HOOC(CH_2)_pO$—, $R_3(CH_2)_qO$— or $R_4[O(CH_2)_2]_rO$—,
wherein n is 0–17, p is 1–10, q is 1–12, r is 1–6,
$R_3$ is 1- or 2- naphthyloxy, 2,3- or 3,4-dihydroxyphenyl, phenyl, phenoxy or substituted phenyl or phenoxy, wherein the substituent is selected from the group consisting of lower alkyl, lower alkoxy, hydroxy, nitro, amino, halo, carboxy or phenyl, and
$R_4$ is lower alkyl;
and pharmaceutically acceptable salts with bases.

The compounds of formula 1 are potent inhibitors of phospholipases $A_2$ (PLA$_2$'s) and are therefore useful in the treatment of diseases, such as psoriasis, inflammatory bowel disease, asthma, allergy, arthritis, dermatitis, gout, pulmonary disease, myocardial ischemia, and trauma induced inflammation, such as spinal cord injury.

DETAILED DESCRIPTION OF THE INVENTION

The invention relates to compounds of the formula

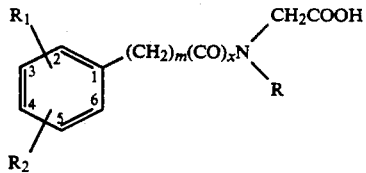

R is hydrogen or —$CH_2COOH$;
m is 0–2,
x is 1–2, with the provision that when x is 2, m is always 0;
$R_1$ is $CH_3(CH_2)_nO$—, $CH_3(CH_2)_nCONH$—, $CH_3(CH_2)_nNHCONH$—, $CH_3(CH_2)_nNHCOO$—, $HOOC(CH_2)_pO$— or $R_3(CH_2)_qO$—;
$R_2$ is hydrogen, carboxy, hydroxy, nitro, amino, $CH_3(CH_2)_nO$—, $CH_3(CH_2)_nCONH$—, $CH_3(CH_2)_nNHCONH$—, $CH_3(CH_2)_nNHCOO$—, $HOOC(CH_2)_pO$—, $R_3(CH_2)_qO$— or $R_4[O(CH_2)_2]_rO$—, wherein n is 0–17, p is 1–10, 1 is 1–12, r is 1–6,
$R_3$ is 1- or 2- naphthyloxy, 2,3- or 3,4-dihydroxyphenyl, phenyl, phenoxy or substituted phenyl or phenoxy, wherein the substituent is selected from the group consisting of lower alkyl, lower alkoxy, hydroxy, nitro, amino, halo, carboxy or phenyl, and
$R_4$ is lower alkyl;
and pharmaceutically acceptable salts with bases.

The compounds of formula 1 are potent inhibitors of phospholipases $A_2$ (PLA$_2$'s) and are therefore useful in the treatment of diseases, such as psoriasis, inflammatory bowel disease, asthma, allergy, arthritis, dermatitis, gout, pulmonary disease, myocardial ischemia, and trauma induced inflammation, such as spinal cord injury.

As used herein, the term "lower alkyl", alone or in combination, denotes a straight or branched chain saturated hydrocarbon containing 1 to 7 carbon atoms, preferably from 1 to 4 carbon atoms, for example, methyl, ethyl, propyl, isopropyl, butyl, dimethylethyl, neopentyl, pentyl, heptyl, and the like.

The term "halogen" denotes all the halogens, for example, bromine, chlorine, fluorine and iodine.

A preferred group of compounds of formula 1 are those wherein the substitution pattern is:

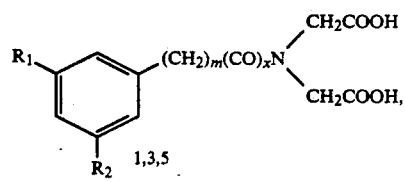

1,3,5

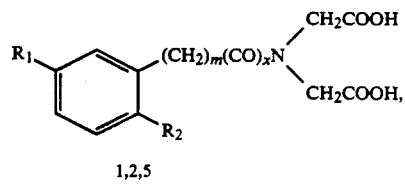

1,2,5

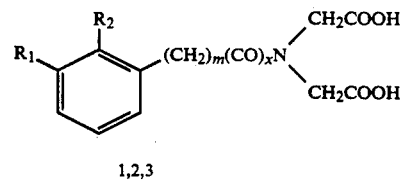

1,2,3 or

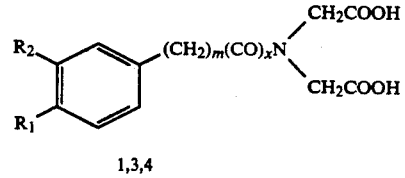

1,3,4 and $R_1$, $R_2$, m and x are as previously described.

A more preferred group of compounds of formula 1 are those in which the substitution pattern is 1,3,5, R is —$CH_2COOH$, m is 0, x is 1–2, $R_1$ and $R_2$ are the same and are $CH_3(CH_2)_nO$—, $CH_3(CH_2)_nCONH$— or $HOOC(CH_2)_pO$— wherein n is 3–17 and p is 5–10.

Another more preferred group of compounds of formula 1 are those in which the substitution pattern is 1,3,5 or 1,2,5, R is —$CH_2COOH$, m is 0, x is 1–2, $R_1$ is $CH_3(CH_2)_nO-$, wherein n is 3-17 or $R_3(CH_2)_qO-$ wherein $R_3$ and q are as previously described, $R_2$ is hydrogen, hydroxyl, nitro, amino, $R_3(CH_2)_qO-$, $R_4[O(CH_2)_2]_rO-$, $HOOC(CH_2)_pO-$, wherein $R_3$, $R_4$, p, q, and r are as previously described.

A most preferred group of compounds of formula 1 are those in which the substitution pattern is 1,3,5, R is —CH$_2$COOH, m is 0, x is 1-2, $R_1$ and $R_2$ are the same and are $CH_3(CH_2)_nO-$, or $CH_3(CH_2)_nCONH-$, wherein n is 9-17.

Another group of most preferred compounds of formula 1 are those in which the substitution pattern is 1,3,5 or 1,2,5, R is —CH$_2$COOH, m is 0, x is 1-2, $R_1$ is $CH_3(CH_2)_nO-$, wherein n is 9-17 or $R_3(CH_2)_qO-$ wherein $R_3$ is phenoxy or phenyl substituted phenoxy, q is 6-12, and $R_2$ is hydrogen, hydroxy or $R_3(CH_2)_qO-$ wherein $R_3$ is phenyl or substituted phenoxy wherein the substituent is benzyloxy or hydroxy and q is 1-3.

The most preferred compounds are the following:

N-(carboxymethyl)-N-[3,5-bis(decyloxy)benzoyl]glycine,

N-(carboxymethyl)-N-[2-hydroxy-5-(octadecyloxy)benzoyl]glycine

N-(carboxymethyl)-N-[2-[4-(octadecyloxy)phenyl]-1,2-dioxoethyl]glycine

N-(carboxymethyl)-N-[5-(octadecyloxy)-2-(phenylmethoxy)benzoyl]glycine

Other preferred compounds are the following:

N-(carboxymethyl)-N-[3-(octadecyloxy)benzoyl]glycine

N-(carboxymethyl)-N-[3,5-bis(tetradecyloxy)benzoyl]glycine

N-(carboxymethyl)-N-[3-[3-(phenoxypropoxy]-5-(octadecyloxy)benzoyl]glycine

N-(carboxymethyl)-N-[3-[3-(3-nitrophenoxy)propoxy]-5-(octadecyloxy)benzoyl]glycine N-(carboxymethyl)-N-[3-[3-(3-aminophenoxy)propoxy]-5-(octadecyloxy)benzoyl]glycine N-(carboxymethyl)-N-[3-(carboxymethoxy)-5-(octadecyloxy)benzoyl]glycine N-(carboxymethyl)-N-[3,5-bis[(10-carboxydecyl)oxy]benzoyl]glycine N-(carboxymethyl)-N-[3-(octadecyloxy)-5-(phenylmethoxy)benzoyl]glycine N-(carboxymethyl)-N-[3-hydroxy-5-(octadecyloxy)benzoyl]glycine N-(carboxymethyl)-N-[3-nitro-5-(octadecyloxy)benzoyl]glycine N-(carboxymethyl)-N-[3-amino-5-(octadecyloxy)benzoyl]glycine N-(carboxymethyl)-N-[3-[2-[2-(2-ethoxyethoxy)ethoxy]ethoxy]-(5-octadecyloxy)benzoyl]glycine N-(carboxymethyl)-N-[3,5-bis(1-oxotetradecylamino)benzoyl]glycine N-(carboxymethyl)-N-[2-[3-(octadecyloxy)phenyl]-1,2-dioxoethyl]glycine N-(carboxymethyl)-N-[[3,5-bis(decyloxy)phenyl]-1,2-dioxoethyl]glycine N-(carboxymethyl)-N-[5-(tetradecyloxy)-2-(phenylmethoxy)benzoyl]glycine N-(carboxymethyl)-N-[5-(decyloxy)-2-(phenylmethoxy)benzoyl]glycine N-[5-[[6-([1,1'-biphenyl]-4-yloxy)hexyl]oxy]-2-(phenylmethoxy)benzoyl]-N-(carboxymethyl)glycine N-(carboxymethyl)-N-[5-[(12-phenoxydodecyl)oxy]-2-(phenylmethoxy)benzoyl]glycine Exemplary of other compounds of the invention are:

N-(carboxymethyl)-N-[5-(octadecyloxy)-2-[(4-hydroxyphenyl)methoxy]benzoyl]glycine N-(carboxymethyl)-N-[5-(octadecyloxy)-2-[(3-hydroxyphenyl)methoxy]benzoyl]glycine N-(carboxymethyl)-N-[5-(octadecyloxy)-2-[(4-nitrophenyl)methoxy]benzoyl]glycine N-(carboxymethyl)-N-[5-(octadecyloxy)-2-[(3-nitrophenyl)methoxy]benzoyl]glycine N-(carboxymethyl)-N-[5-(octadecyloxy)-2-[(4-aminophenyl)methoxy]benzoyl]glycine N-(carboxymethyl)-N-[5-(octadecyloxy)-2-[(3-aminophenyl)methoxy]benzoyl]glycine N-(carboxymethyl)-N-[5-(octadecyloxy)-2-[(4-chlorophenyl)methoxy]benzoyl]glycine N-(carboxymethyl)-N-[5-(octadecyloxy)-2-[(3-fluorophenyl)methoxy]benzoyl]glycine N-(carboxymethyl)-N-[3-[3-(2,3-dihydroxyphenyl)propoxy]-5-(octadecyloxy)benzoyl]glycine N-(carboxymethyl)-N-[3-[6-(2,3-dihydroxyphenyl)hexyloxy]-5-(octadecyloxy)benzoyl]glycine N-(carboxymethyl)-N-[2-[6-(2,3-dihydroxyphenyl)hexyloxy]-5-(octadecyloxy)benzoyl]glycine N-(carboxymethyl)-N-[2-[(3-octadecyloxy)-5-[6-(2,3-dihydroxyphenyl)hexyloxy]phenyl]1,2-dioxoethyl]glycine N-[3,5-bis(decyloxy)benzoyl]glycine N-[3,5-bis(tetradecyloxy)benzoyl]glycine N-[2-hydroxy-5-(octadecyloxy)benzoyl]glycine N-[5-(octadecyloxy)-2-(phenylmethoxy)benzoyl]glycine N-[3,5-bis(1-oxotetradecylamino)benzoyl]glycine N-[2-[3-(octadecyloxy)phenyl]-1,2-dioxoethyl]glycine N-(carboxymethyl)-N-[2,5-bis(tetradecyloxy)benzoyl]glycine N-(carboxymethyl)-N-[2,5-bis(decyloxy)benzoyl]glycine N-(carboxymethyl)-N-[3-[3-(4-hydroxyphenyl)propoxy]-5-(octadecyloxy)benzoyl]glycine N-(carboxymethyl)-N-[3-[3-(4-methoxyphenyl)propoxy]-5-(octadecyloxy)benzoyl]glycine N-(carboxymethyl)-N-[3-[3-(4-chlorophenyl)propoxy]-5-(octadecyloxy)benzoyl]glycine N-(carboxymethyl)-N-[3-[3-(4-fluorophenyl)propoxy]-5-(octadecyloxy)benzoyl]glycine N-(carboxymethyl)-N-[[2,3-bis(decyloxy)phenyl]carbonyl]glycine N-(carboxymethyl)-N-[[2,3-bis(tetradecyloxy)phenyl]carbonyl]glycine N-(carboxymethyl)-N-[3-(octadecyloxy)-2-(phenylmethoxy)benzoyl]glycine N-(carboxymethyl)-N-[3-(octadecyloxy)-2-(4-hydroxyphenylmethoxy)benzoyl]glycine N-(carboxymethyl)-N-[3,5-bis[[(decylamino)carbonyl]amino]benzoyl]glycine N-(carboxymethyl)-N-[3,5-bis[[(tetradecylamino)carbonyl]amino]benzoyl]glycine N-(carboxymethyl)-N-[3,5-bis[[(decylamino)carbonyl]oxy]benzoyl]glycine N-(carboxymethyl)-N-[3,5-bis[[(tetradecylamino)carbonyl]oxy]benzoyl]glycine The compounds of formula 1 can be prepared as set forth in Schemes 1-5.

REACTION SCHEME 1

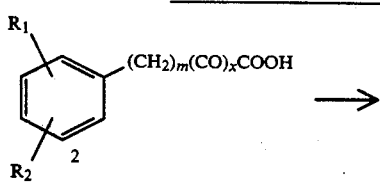

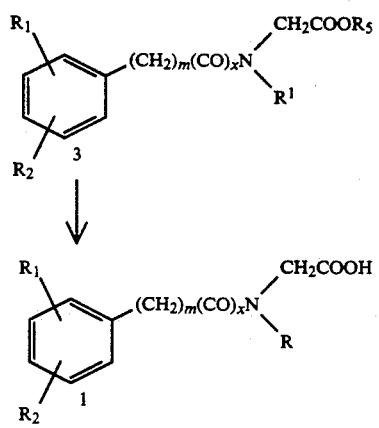

wherein R$_5$ is lower alkyl or benzyl; R' is —CH$_2$COOR$_5$ or H; X is 0–1 and R, R$_1$, R$_2$ and m are as previously described.

In Reaction Scheme 1, an acid of formula 2 can be converted to the corresponding acid chloride by treatment with thionyl chloride, either without an added solvent or with an inert solvent, such as benzene or toluene, sometimes with added pyridine at temperatures of from 50°–110°. Alternatively, treatment of an acid of formula 2 with oxalyl chloride in a solvent such as methylene chloride, containing small amounts of DMF (dimethyl formamide), at a temperature in the range of from 10° to 40°, also provides the corresponding acid chlorides.

An acid chloride so obtained is not purified but is converted directly to the corresponding intermediates of formula 3 by treatment with dimethyl iminodiacetate, diethyl iminodiacetate, dibenzyl iminodiacetate or glycine methyl ester in a solvent such as THF (tetrahydrofuran) or methylene chloride in the presence of an organic base, such as triethylamine, at temperatures of from 0°–30°.

A compound of formula 3 can be converted to the corresponding compound of formula 1 of the invention by treatment with an alkali metal hydroxide, such as sodium hydroxide, in a solvent, such as methanol or ethanol, with added dioxane to improve solubility if required, at a temperature in the range of from 25°–80°. If R$_5$ is a benzyl group, a compound of formula 3 can be converted to the corresponding compound of formula 1 by hydrogenolysis carried out by stirring or shaking in a hydrogen atmosphere using a catalyst such as palladium, in a solvent, such as ethyl acetate or THF, at temperature in the range of from 20°–50°.

The intermediate acids (6 and 9) required for the preparation of the compounds 1 of the invention (wherein x is 1) can be prepared in accordance with Reaction Schemes 2 and 3, as described in the Examples and as further exemplified in U.S. patent application Ser. No. 914,825, filed Jul. 15, 1992.

REACTION SCHEME 2

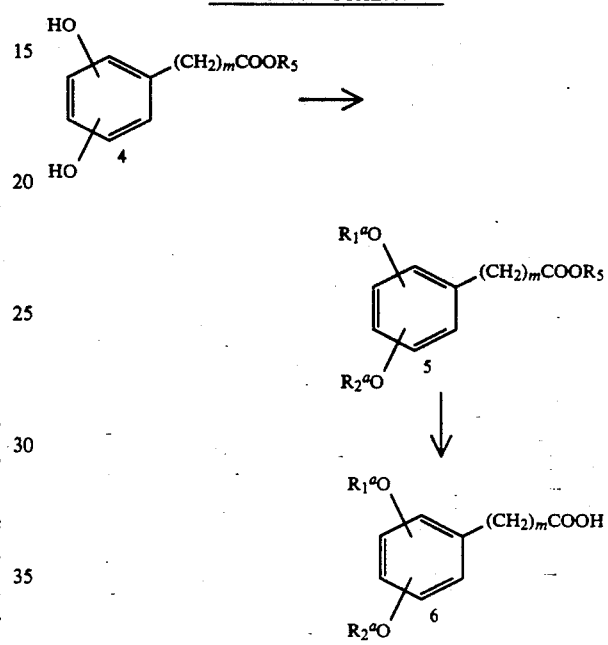

wherein R$_5$ is lower alkyl or benzyl; R$_1{}^a$ and R$_2{}^a$ are the same and are CH$_3$(CH$_2$)$_n$—, R$_3$(CH$_2$)$_q$— or R$_4$OOC(CH$_2$)$_p$— and n, m, p and q are as previously described.

In Reaction Scheme 2 compounds of formula 4, which are known compounds, can be converted to the corresponding dialkylated ester of formula 5 (wherein R$_1{}^a$ and R$_2{}^a$ are the same) by treatment with an excess of the required halide in a solvent such as acetone, DMF or mixtures thereof, at a temperature in the range of from 50° to 100° in the presence of an alkali metal carbonate, such as potassium carbonate. Conversion of a compound of formula 5 to the corresponding acid of formula 6 can be accomplished by base hydrolysis using an alkali metal hydroxide, such as sodium hydroxide, in a solvent, such as methanol or ethanol, with added dioxane to improve solubility if required, at a temperature in the range of from 25° to 80°. Hydrogenolysis (when R$_5$ is benzyl) of a compound of formula 5 under standard conditions by shaking or stirring in a hydrogen atmosphere using a catalyst, such as palladium, in a solvent, such as ethyl acetate or THF, at a temperature in the range of from 20°–50°, also provides the corresponding compound of formula 6.

REACTION SCHEME 3

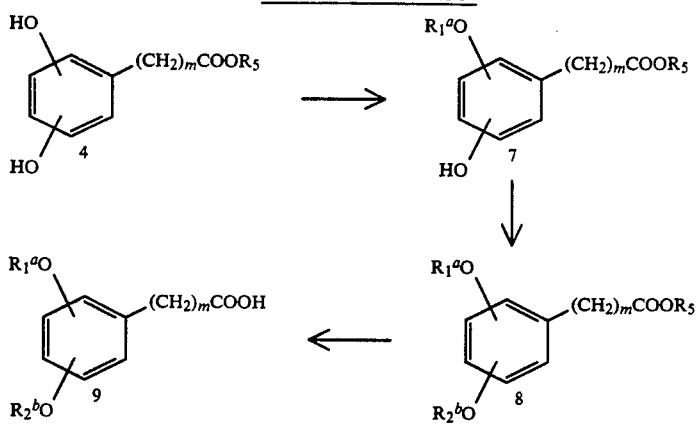

wherein $R_5$ is lower alkyl or benzyl; $R_1{}^a$ is $CH_3(CH_2)_n-$, $R_3(CH_2)_q-$ or $R_4OOC(CH_2)_p-$; $R_2{}^b$ is $CH_3(CH_2)_n-$, $R_3(CH_2)_q-$, $R_4OOC(CH_2)_p-$, or $R_4[O(CH_2)_2]_r$; n, m, p, q and r are as previously described.

In Reaction Scheme 3, a compound of formula 4 can also be converted to the corresponding monoalkylated ester of formula 7 by treatment with one equivalent of the required halide under the conditions previously described above. The corresponding compounds of formula 7 then can be converted to the corresponding compounds of formula 8 by treatment with a different halide under the same reaction conditions. Finally, base hydrolysis or hydrogenolysis under conditions described above provides the corresponding intermediate acids of formula 9.

wherein R' is $CH_2COOR_4$ or H; and $R_1{}^c$ and $R_2{}^c$ are the same and are $CH_3(CH_2)_n-$ or $CH_3(CH_2)_nNH-$ and $R_4$. R and n are as previously described.

In Reaction Scheme 4, a known acid chloride of formula 10 is treated with dimethyl iminodiacetate, diethyl iminodiacetate or glycine methyl ester in a solvent, such as methylene chloride or THF, in the presence of an organic base, such as triethylamine, at a temperature in the range of from 0° to 30° C., to give the corresponding compound of formula 11. Hydrogenation of a compound of formula 11 by shaking under hydrogen pressure using a catalyst, such as palladium, in a solvent, such as ethyl acetate or THF, gives the corresponding compounds of formula 12. A compound of formula 12 can be converted to the corresponding compound of formula 13 by treatment with the desired acid chloride or isocyanate in a solvent, such as THF in

REACTION SCHEME 4

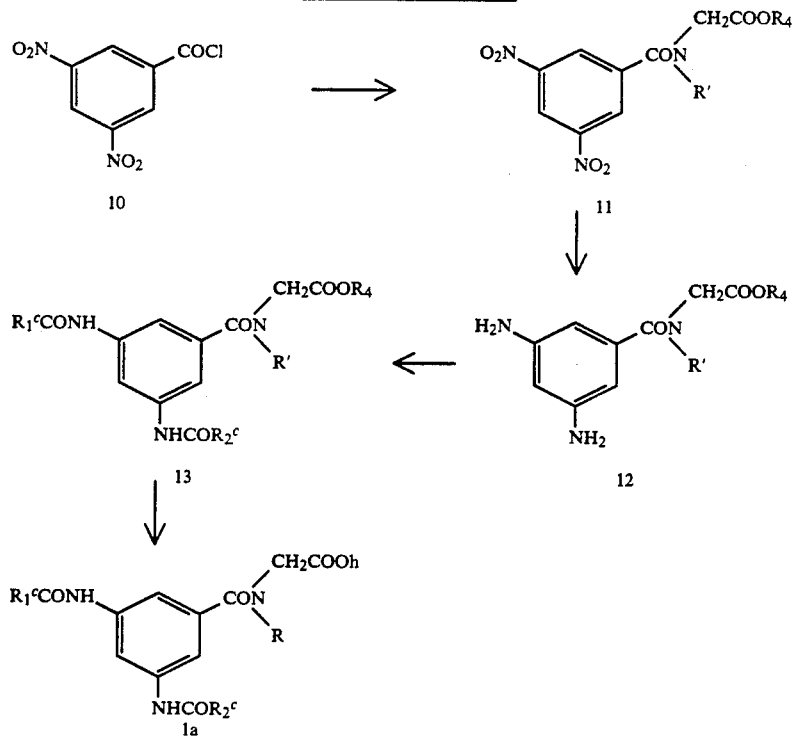

the presence of an organic base, such as triethylamine, at temperature in the range of from 0° to 30° C. Finally, base hydrolysis of a compound of formula 13 by treatment with an alkali metal hydroxide, such as sodium hydroxide, in a solvent, such as methanol or ethanol, at a temperature in the range of from 25°–80° C., provides the corresponding compounds 1a of the invention.

REACTION SCHEME 5

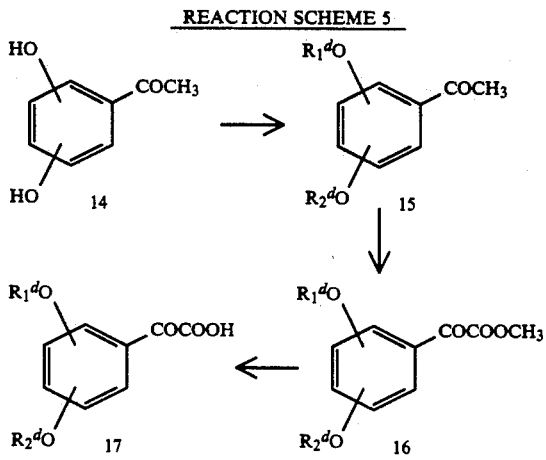

wherein $R_1^d$ and $R_2^d$ are the same and are $CH_3(CH_2)_n-$ or $R_3(CH_2)_q-$.

REACTION SCHEME 6

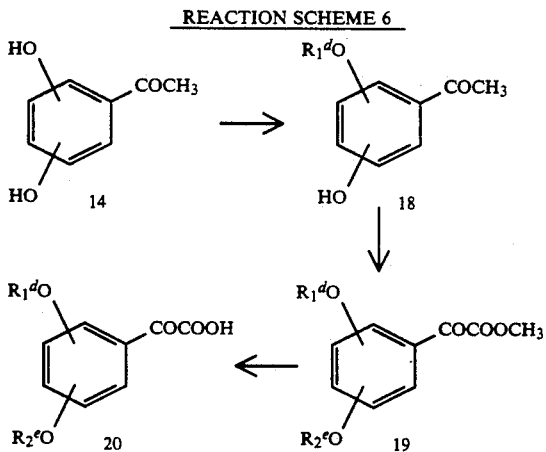

wherein $R_1^d$ is $CH_3(CH_2)_n-$ or $R_3(CH_2)_q-$ and $R_2^e$ is $CH_3(CH_2)_n-$, $R_3(CH_2)_q-$ or $R_4[O(CH_2)_2]_r-$.

The procedures described in Reaction Schemes 5 and 6 can be used to prepare the intermediate acids (17 and 20) required for synthesis of compounds of formula 1, wherein x is 2 and m is 0. A known compound of formula 14 can be converted to the corresponding alkylated acetophenone of formula 15 by treatment with an excess of the required halide under conditions described in Scheme 2. Oxidation of a compound of formula 15 can be accomplished by treatment with selenium dioxide in pyridine at a temperature in the range of from 80° to 110°. The corresponding crude alpha-keto acid obtained is treated with methyl chloroformate to yield the corresponding alpha-keto ester of formula 16. Base hydrolysis of a compound of formula 16 using an alkali metal hydroxide, such as sodium hydroxide, in a solvent, such as methanol or ethanol, at a temperature in the range of from 25° to 80°, provides the corresponding compounds of formula 17.

A known compound of formula 14 can also be converted to the corresponding compounds of formula 18 by sequential treatment with different halides as described in Scheme 3 followed by selenium dioxide oxidation, esterification to give the corresponding compound of formula 19 and base hydrolysis as described above to yield the corresponding compound of formula 20.

The invention also relates to salts of the compounds of formula 1 which lend themselves to salt formation with a base. Salts of the compounds of formula 1 are prepared by the reaction with a base having a non-toxic, pharmacologically acceptable cation. In general, any base which will form a salt with a carboxylic acid and whose pharmacological properties will not cause an adverse physiological effect is within the scope of this invention.

Suitable bases thus include, for example, the alkali metal and alkaline earth metal hydroxides, carbonates or the like, for example, calcium hydroxide, sodium hydroxide, sodium carbonate, potassium carbonate or the like, ammonia, primary, secondary and tertiary amines, such as monoalkylamines, dialkylamines, trialkylamines, for example, methylamine, diethylamine, triethylamine or the like, nitrogen containing heterocyclic amines, for example, piperidine or the like. A salt thus produced is the functional equivalent of the corresponding acids of formula 1 and one skilled in the art will appreciate that the variety of salts embraced by the invention is limited only by the criterion that a base employed in forming the corresponding salts be both non-toxic and physiologically and pharmaceutically acceptable.

The useful activity of the compounds of formula 1 as phospholipase $A_2$ ($PLA_2$) inhibitors can be demonstrated as hereinafter set forth.

The compounds of formula 1 are potent inhibitors of phospholipases $A_2$ ($PLA_2$'s) and are therefore useful in the treatment of diseases, such as psoriasis, inflammatory bowel disease, asthma, allergy, arthritis, dermatitis, gout, pulmonary disease, myocardial ischemia, and trauma induced inflammation, such as spinal cord injury.

Assay for Inhibition of HSF-$PLA_2$ In Vitro

The $PLA_2$ used in this test is the extracellular enzyme obtained from human synovial fluid (HSF-$PLA_2$).

The assay for HSF-$PLA_2$ activity was a modification of the described method [Franson R., Dobrow R., Weiss, J., Elsbach P., and Weglick W. B., J. Lipid Res., 19, 18–23 (1978)] which was conducted using [1-$^{14}$C]-oleate-labelled $E.$ $coli$ substrate in excess at a final concentration of 20,000 dpm/ml. This was equivalent to 18.2 mM of cell membrane phospholipid phosphorus and $2 \times 10^9$ autoclaved $E.$ $coli$/ml. The optimal conditions which were developed for the assay of HSF-$PLA_2$ inhibitors are summarized as follows. A total volume of 0.5 ml of reaction mixture typically had the following final composition: substrate (20,000 dpm/ml); enzyme (0.1% HSF, v/v); 2 mM $CaCl_2$; 150 mM Na$^+$; 50 mM sodium HEPES buffer, pH 7.3; and 1% dimethyl sulfoxide (DMSO, used to solubilize test inhibitors) in the presence or absence of inhibitor. The reaction was initiated by the addition of HSF-$PLA_2$ and duplicate samples of the mixture were incubated in $13 \times 100$ mm glass tubes with shaking for 30 minutes at 37° C. The reaction was terminated by the addition of 2.5 ml of chloroform-methanol (1 to 1.5, v/v). The extraction of lipids from the stopped reaction mixture was conducted by the further additions of 0.5 ml of chloroform and 1 ml of water with mixing. After centrifuging, the lower chloroform phase was transferred to smaller glass tubes and the solvent was evaporated to dryness with a nitrogen stream. The extracted lipid residue was redissolved in 50 ml of a solution containing carrier oleic acid (0.2 mg/ml) in chloroform-methanol [9 to 1, v/v]). The whole lipid extract was applied to a preactivated (30 minutes at 110° C.) silica gel-impregnated glass fiber thin layer chromatography sheet (ITLC type SG sheet from Gelman Sciences Inc., Ann Arbor, Mich.) using hexane-acetic acid (100 to 1, v/v) as the developing solvent. This TLC system rapidly (6 minutes) resolved the enzymatically released product, $^{14}$C-oleic acid, from the unreacted $^{14}$C-phospholipid substrate. The unsaturated lipids were located on the chromatogram by a brief exposure to iodine vapor. The oleic acid zone ($R_f$ value 0.95) and phospholipid zone (origin) were cut out, chopped into small pieces, shaken with 2 ml of ethanol-water (80 to 20, v/v) and 15 ml of Aquasol and counted for radio-activity. A control incubation of substrate in the absence of HSF-PLA$_2$ was performed in each experiment. The PLA$_2$ activity of the human synovial fluid was corrected for this small control value. In the absence of inhibitors, these optimal conditions resulted in approximately 18% hydrolysis of substrate (corrected for a substrate blank of <2%). The specific activity of PLA$_2$ in the pooled human synovial fluid under the optimal assay conditions was 49.2 nmoles [1-$^{14}$C]-oleic aid released hour$^{-1}$ mg$^{-1}$. The IC$_{50}$ ($\mu$M concentration of test compound that produces 50% inhibition of PLA$_2$ activity) was determined for each test compound. The results are reported in Tables I and II.

Croton Oil Mouse Ear Edema Test

The croton oil-induced mouse ear edema test, a model of irritant-induced contact dermatitis, has been used for evaluation of the PLA$_2$ inhibitors by the topical route of administration. This test was carried out as described in the following references:

Weirich, E. G., Longauer, J. K. and Kirkwood, A. A. Arch. Dermatol. Res. 259: 141–149, 1977.

Tubaro, A., Dri, P., Delbello, G., Zilli, C. and Della Loggia, R. Agents and Actions, 17: 347–349, 1985.

The major active ingredient in croton oil is the tumor promoter 12-O-tetradecanoylphorbol-13-acetate (TPA) and the topical application of TPA to mouse skin has been reported to cause an increase in epidermal PGE$_2$ production as well as an increase in epidermal cell membrane PLA$_2$ activity. Indomethacin, an inhibitor of prostaglandin synthesis, prevented the TPA-mediated increase in epidermal PGE$_2$ levels as well as the TPA-mediated induction of epidermal cell ornithine decarboxylase. Furthermore, the application of PGE$_2$ to mouse skin countered the inhibitory effect of indomethacin upon TPA-stimulated cellular proliferation. Taken together these data suggest that the croton oil mouse ear edema test is a valid model for the topical evaluation of PLA$_2$ inhibitors.

Twenty five $\mu$l of a 1% croton oil solution [dissolved in a mixture of pyridine/water/diethyl ether at a ratio of 5/20/75 (croton oil vehicle)] are applied to the outer side of the right ear of 3-4 week old male CD-1 mice (8 animals per group). The test compounds are dissolved directly in the 1% croton oil solution at various concentrations and coapplied. Control animals receive 25 $\mu$l of croton oil vehicle on the right ear. Biopsy punches are removed at 6 hours from the right ear of the animals using a 6 mm skin trephine (Roboz, Washington, D.C.) and the wet weight of the ear punches is determined. The weight of the biopsy punches is a measure of ear inflammation, primarily edema. The data are expressed as percent inhibition relative to control groups.

The in vivo activity of representative compounds of formula 1 in the croton oil ear edema test are reported in Table I.

Statistical analysis of the mean edema values of the control versus the treated groups is performed using Student's t-test. The significance of changes from mean value for vehicle-treated animals is as follows (*$p<0.05$, $p<0.01$, *$p<0.005$, ns/not significant).

TPA Induced Mouse Ear Edema Test

The TPA-induced mouse ear edema test, a model of irritant-induced contact dermatitis is described in the following reference: J. M. Young, B. M. Wagner and D. A. Spires, J. Invest. Dermatology 80, 48–52 (1983).

For this test, 10 $\mu$l of 12-O-tetradecanoylphorbol-13-acetate (TPA), dissolved in a vehicle of pyridine: water: diethylether (20:5:75), was applied to the outside of the right ear of 3-4 week old male CD-1 mice (8 animals per group). The test compounds were dissolved in the same vehicle and 10 $\mu$l was applied to the inside of the same ear 30 minutes prior to the application of TPA. Ear punches (6 mm) were removed at 6 hours after TPA application, weighed and assayed for myeloperoxidase (MPO) activity as described in the following reference: P. P. Bradley, D. A. Priebat, R. D. Christensen and G. Rothstein, J. Invest. Dermatology 78, 206–209 (1982). The wet weight of the ear biopsy punches is a measure of the ear edema and the level of MPO activity in the ear punches is an indicator of neutrophil infiltration. The data are expressed as percent inhibition in drug-treated animals relative to the control group. Table II sets forth the percentage inhibition of edema by representative compounds of the invention in this test. Table III sets forth the percentage inhibition of myeloperoxidase by representative compounds of the invention in this test.

TABLE I

| Ex No | Name | % Inhib of HSF-PLA$_2$ | % Inhib of Croton Oil Mouse Ear Edema (1 mg) |
|---|---|---|---|
| 4 | N-(carboxymethyl)-N-[3-(octadecyloxy)benzoyl]glycine | 50 (5.8 $\mu$M) | 17* |
| 5 | N-(carboxymethyl)-N-[3-(tetradecyloxy)benzoyl]glycine | 13 (5 $\mu$M) | 10ns |
| 6 | N-(carboxymethyl)-N-[3-(decyloxy)benzoyl]glycine | 8 (5 $\mu$m) | 47** |
| 9 | N-(carboxymethyl)-N-[3-(1-oxooctadecyl)amino)benzoyl]glycine | 8 (5 $\mu$M) | 20** |

TABLE I-continued

| Ex No | Name | % Inhib of HSF-PLA$_2$ | % Inhib of Croton Oil Mouse Ear Edema (1 mg) |
|---|---|---|---|
| 11 | N-(carboxymethyl)-N-[3,5-bis(decyloxy)benzoyl]glycine | 50 (6 μM) | 70*** |
| 13 | N-(carboxymethyl)-N-[3,5-bis(tetradecyloxy)bnezoyl]glycine | 27 (1 μM) | 60*** |
| 18 | N-(carboxymethyl)-N-[3-[3-(phenoxypropoxy]-5-(octadecyloxy)benzoyl]glycine | 72 (5 μM) | 59*** |
| 20 | N-(carboxymethyl)-N-[3-[3-(4-methoxyphenoxypropoxy]-5-(octadecyloxy)benzoyl]glycine | 18 (1 μM) | 21ns |
| 22 | N-(carboxymethyl)-N-[3-[3-(3-nitrophenoxy)propoxy]-5-(octadecyloxy)benzoyl]glycine | 60 (5 μM) | 54*** |
| 23 | N-(carboxymethyl)-N-[3-[3-(3-aminophenoxy)propoxy]-5-(octadecyloxy)benzoyl]glycine | 50 (5 μM) | 21* |
| 25 | N-(carboxymethyl)-N-[3-[2-(2-naphthyloxy)ethyloxy]-5-(octadecyloxy)]benzoyl]glycine | −16 (5 μM) | 44** |
| 30 | N-(carboxymethyl)-N-[3-carboxy-5-(octadecyloxy)benzoyl]glycine | 23 (5 μM) | 1ns |
| 33 | N-(carboxymethyl)-N-[3-(carboxymethoxy)-5-(octadecyloxy)benzoyl]glycine | 29 (1 μM) | 71*** |
| 35 | N-(carboxymethyl)-N-[3,5-bis[(10-carboxydecyl)oxy]benzoyl]glycine | 5 (5 μM) | 50** |
| 38 | N-(carboxymethyl)-N-[3-(octadecyloxy)-5-(phenylmethoxy)benzoyl]glycine | 55 (5 μM) | 35** |
| 39 | N-(carboxymethyl)-N-[3-hydroxy-5-(octadecyloxy)benzoyl]glycine | 20 (5 μM) | 47* |
| 43 | N-(carboxymethyl)-N-[3-nitro-5-(octadecyloxy)benzoyl]glycine | 10 (5 μM) | 48** |
| 44 | N-(carboxymethyl)-N-[3-amino-5-(octadecyloxy)benzoyl]glycine | 34 (5 μM) | 35** |
| 48 | N-(carboxymethyl)-N-[3-[2-[2-(2-ethoxyethoxy)ethoxy]ethoxy]-5-(octadecyloxy)benzoyl]glycine | 36 (5 μM) | 19* |
| 51 | N-(carboxymethyl)-N-[3,4-bis(tetradecyloxy)benzoyl]glycine | 38 (5 μM) | 15ns |
| 62 | N-(carboxymethyl)-N-[2-hydroxy-5-(octadecyloxy)benzoyl]glycine | 50 (5.8 μM) | 65*** |
| 65 | N-(carboxymethyl)-N-[2-[4-(octadecyloxy)phenyl]-1,2-dioxoethyl]glycine | 74 (1 μM) | 44*** |
| 69 | N-(carboxymethyl)-N-[2-[3-(octadecyloxy)phenyl]-1,2-dioxoethyl]glycine | 57 (5 μM) | 28* |
| 73 | N-(carboxymethyl)-N-[[3,5-bis(decyloxy)phenyl]-1,2-dioxoethyl]glycine | 62 (5 μM) | 26ns |
| 74 | N-[3-(octadecyloxy)benzoyl]glycine | 23 (5 μM) | 33* |
| 76 | N-(carboxymethyl)-N-[3-octadecyloxy)phenylacetyl]glycine | 45 (5 μM) | 38** |
| 78 | (E)-N-(carboxymethyl)-N-[3-[(3-octadecyloxy)phenyl]-1-oxo-2-propenyl]glycine | 68 (5 μM) | 48*** |
| 79 | N-(carboxymethyl)-N-[3-[(3-octadecyloxy)phenyl]-1-oxopropyl]glycine | 70 (5 μM) | 11ns |
| 81 | N-(carboxymethyl)-N-[5-(octadecyloxy)-2-(phenylmethoxy)benzoyl]glycine | 42 (5 μM) | 74*** |

TABLE II

| Ex No | Name | % Inhib of HSF-PLA$_2$ | % Inhib of TPA Mouse Ear Edema (1 mg) |
|---|---|---|---|
| 81 | N-(carboxymethyl)-N-[5-(octadecyloxy)-2-(phenylmethoxy)benzoyl]glycine | 42 (5 μM) | 60*** (0.3 mg) |
| 86 | N-(carboxymethyl)-N-[5-(tetradecyloxy)-2-phenylmethoxy)benzoyl]glycine | 70 (10 μM) | 47*** |
| 91 | N-(carboxymethyl)-N-[5-(decyloxy)-2-(phenylmethoxy)benzoyl]glycine | 70 (10 μM) | 59*** |
| 95 | N-(carboxymethyl)-N-[5-(octadecyloxy)-2-(3-phenylpropoxy)benzoyl]glycine | 71 (10 μM) | 55*** |
| 99 | N-(carboxymethyl)-N-[5-(octadecyloxy)- | 86 (10 μM) | 50*** |

TABLE II-continued

| Ex No | Name | % Inhib of HSF-PLA$_2$ | % Inhib of TPA Mouse Ear Edema (1 mg) |
|---|---|---|---|
| 100 | 2-[3-[4-(phenylmethoxy)phenoxy]propoxy]benzoyl]glycine N-(carboxymethyl)-N-[[2-[3-(4-hydroxyphenoxy)propoxy]-5-(octadecyloxy)phenyl]benzoyl]glycine | 77 (10 μM) | 65*** |
| 105 | N-[5-[[6-([1,1'-biphenyl]-4-yloxy)hexyl]oxy]-2-(phenylmethoxy)benzoyl]-N-(carboxymethyl)glycine | 38 (10 μM) | 67*** |
| 110 | N-(carboxymethyl)-N-[5-[(12-phenoxydodecyl)oxy]-2-(phenylmethoxy)benzoyl]glycine | 61 (10 μM) | 57*** |
| 114 | N-(carboxymethyl)-N-[1,2-dioxo-2-[4-[(12-phenoxydodecyl)oxy]phenyl]ethyl]glycine | 35 (10 μM) | 37*** |

TABLE III

| Ex No | Name | % Inhib of Myeloperoxidase Mouse Ear Edema (1 mg) |
|---|---|---|
| 81 | N-(carboxymethyl)-N-[5-(octadecyloxy)-2-(phenylmethoxy)benzoyl]glycine | 75 (0.3 mg) |
| 86 | N-(carboxymethyl)-N-[5-(tetradecyloxy)-2-(phenylmethoxy)benzoyl]glycine | 63 |
| 91 | N-(carboxymethyl)-N-[5-(decyloxy)-2-(phenylmethoxy)benzoyl]glycine | 78 |

Phospholipase A$_2$ Rat Paw Edema

Representative compounds of the invention were tested in rats to determine their ability to inhibit the acute inflammatory response induced by the injection of snake venom phospholipase A$_2$. Test compounds were administered intraperitoneally or orally to groups of seven Lewis rats (~200 gm) 1 hr prior to phospholipase A$_2$ administration. The test compounds were dissolved in dimethyl sulfoxide for intraperitoneal administration and dissolved or suspended in Labrafil M-1944CS for oral administration. At 0 hr, 5 ug (10 units) of purified phospholipase A$_2$ from Naja naja venom (Sigma Chem. Co.) dissolved in 0.1 mL of pyrogen free saline was injected subplantarly into the right hind paw to elicit the inflammatory response. The volume (in mL) of the right hind paw was measured by immersion of the paw to the level of the lateral malleolus in an aqueous plethysmometer immediately prior to the injection of phospholipase A$_2$ and then at 0.5, 2 and 4 hr after phospholipase A$_2$ injection. The paw edema was calculated by subtracting the zero time reading from the readings taken after injection. The percent change of the edema volume from the vehicle treated control was calculated to determine the activity of the test compound. Results obtained with representative compounds of the invention in this test are set forth in Table IV.

Rat Carrageenan Paw Edema

Representative compounds of the invention were tested in rat carrageenan-induced paw edema to determine their ability to inhibit this acute inflammatory response. Test compounds were administered intraperitoneally or orally to groups of seven Lewis rats (~200 gm) 1 hr prior to carrageenan administration. The test compounds were dissolved in dimethyl sulfoxide for intraperitoneal administration and dissolved or suspended in Labrafil M-19944CS for oral administration. At 0 hour, 0.1 mL of 1% carrageenan dissolved in pyrogen free silane was injected subplanetary into the right hind paw to elicit the inflammatory response. The volume (in mL) of the right hind paw was measured by immersion of the paw to the level of the lateral malleolus in an aqueous plethysmometer immediately prior to the injection of carrageenan and then at 1, 2 and 4 hr after carrageenan injection. The paw edema was calculated by subtracting the zero time reading from the readings taken after injection. The percent change of the edema volume from the vehicle treated control was calculated to determine the activity of the test compound. Statistical analysis of the mean paw edema values of the control versus the treated groups was performed using Student's t-test. Results obtained with representative compounds of the invention in this test are also set forth in Table IV.

TABLE IV

| Ex No | Name | % Inhib of PLA$_2$ Paw Edema 2 hr 30 mg/kg ip | % Inhib of Carrageenan Paw Edema 2 hr 30 mg/kg ip |
|---|---|---|---|
| 11 | N-(carboxymethyl)-N-[(3,5-bis(decyloxy)benzoyl]glycine | 0 | 50** (50 mg/kg) |
| 62 | N-(carboxymethyl)-N-[2-hydroxy-5-(octadecyoxy)benzoyl]glycine | 60** | 57** |
| 4 | N-(carboxymethyl)-N-[3-(octadecyloxy)benzoyl]glycine | 35* | 50** |
| 22 | N-(carboxymethyl)-N-[3-[3-(3-nitrophenoxy)propoxy]-5-(octadecyloxy)benzoyl]glycine | 64** | NT |
| 23 | N-(carboxymethyl)-N-[3-[3-(3-aminophenoxy)propoxy]-5-(octadecyloxy)benzoyl]glycine | 40** | NT |
| 48 | N-(carboxymethyl)-N-[3-[2-[2-(2-ethoxyethoxy)ethoxy]ethoxy]-5-(octadecyloxy)benzoyl]glycine | 43** | 76** |
| 56 | N-(carboxymethyl)-N-[3,5-bis(1-oxo tetradecylamino)benzoyl]glycine | 57** | 26* (100 mg/kg po) |
| 65 | N-(carboxymethyl)-N-[2-[4-(octadecyloxy)phenyl]-1,2-dioxoethyl]glycine | 71** | 71** |
| 73 | N-(carboxymethyl)-N-[[3,5-bis(decyloxy)phenyl]1,2-dioxo-ethyl]glycine | 32** | 56** |

Established Adjuvant Arthritis Test

Representative compounds of the invention were tested in the standard adjuvant arthritis model in rats, induced by Freunds complete adjuvant, as described by C. E. Brinkerhoff, J. W. Coffey and A. C. Sullivan, Science, 221, 756-758 (1983). The results obtained are set forth in Table V.

Acetic Acid-Induced Colitis in Rats

The rat acetic acid-induced colitis bioassay has been described by J. E. Krawisz, et al. in Amer. J. Proc. Gastro. Col. Rec. Surg. 31, 11-18 (1980), and by P. Sharon and W. F. Stenson in Gastroenterology 88, 55-63 (1985) and 86, 453-460 (1984). Acetic acid-induced colitis is characterized by the movement of inflammatory cells into the colon, with the number of such cells in the mucosa being measured by the activity of myeloperoxidase, a marker enzyme for these cells. Positive desirable activity is indicated by a reduction in the high levels of myeloperoxidase caused by acetic acid. Male rats (Sprague-Dawley), weighing 150 to 300 g, were pretreated twice daily for two days with either the vehicle (water or dimethylsulfoxide) or the test inhibitor compound suspended in water or dissolved in dimethylsulfoxide and orally administered. On the third day, the animals were dosed the same as on the previous two days, anesthetized with metofane, and 2 ml of 2.5% acetic acid was injected by syringe into the colonic lumen, followed immediately by 3 ml of air and a rinse consisting of 3 ml of phosphate-buffered saline (the acetic acid is present in the lumen for a sufficient period to cause inflammation without producing severe necrosis or irreversible damage). The animals were administered a second dose of the test compound in the same amount about 16 hours later. Then 24 hours after the acetic acid treatment, the animals were sacrificed. The colonic mucosa was surgically removed and homogenized in an aqueous buffer at pH 6 with a Tissumizer or similar device and myeloperoxidase was measured in the homogenate using o-phenyl enediamine as a chromagen, as described by A. Voller, D. E. Bidwell and A. Bartlett in "The Enzyme Linked Immunosorbent Assay (ELISA)", Zoological Soc., London, 1979, pages 29-30. Control animals were pretreated with the vehicle and saline in place of acetic acid. A compound of the invention was tested, and the results obtained are set forth in Table V.

TABLE V

| Ex | Name | Dose mg/kp ip | | |
|----|------|---------------|---|---|
| ESTABLISHED ADJUVANT ARTHRITIS TEST | | | | |
| | | | Change in Paw Volume in ml | |
| | | | Treated | Control |
| 4 | N-(carboxymethyl)-N-[3-(octadecyloxy)benzoyl]glycine | 10 | −0.14 ± 0.06** | 0.48 |
| 62 | N-(carboxymethyl)-N-[2-hydroxy-5-(octadecyloxy)benzoyl]glycine | 30 | −0.11 ± 0.06** | 0.86 |
| 65 | N-(carboxymethyl)-N-[2-[4-(octadecyloxy)phenyl]-1,2-dioxoethyl]glycine | 10 | −0.07 ± 0.08* | 0.28 |
| RAT ACETIC ACID COLITIS TEST | | | | |
| | | | % Inhib of Myeloperoxidase Accumulation | |
| 4 | N-(carboxymethyl)-N-[3-(octadecyloxy)benzoyl]glycine | 10 mg/kg po | 112 ± 53 | |

In practice of the invention, the dose of a compound of formula 1 or a salt thereof to be administered and the frequency of administration will be dependent on the potency and duration of activity of the particular compound of formula 1 or salt to be administered and on the route of administration, as well as the severity and nature of the condition and age of the mammal to be treated and the like. Oral doses of a compound of formula 1 or a salt thereof contemplated for use in practicing the invention can be in the range of from 10 mg to about 2.0 g per day, preferably about 50 mg to about 1 g per day, either as a single dose or in divided doses. For topical use a compound of formula 1 or salt thereof contemplated for use in practicing the invention is present in the topical composition in the range of from about 1 to about 10%, preferably from about 2 to about 5%.

A compound of formula 1, or a salt or a composition containing a therapeutically effective amount of a compound of formula 1, or a salt thereof can be administered by methods well known in the art. Thus, a compound of formula 1, or a salt thereof can be administered either singly or with other pharmaceutical agents, for example, antihistamines, mediator release inhibitors, methyl xanthines, beta agonists or antiasthmatic steroids such as prednisone and prednisolone, orally, parenterally, rectally, or by inhalation, for example in the form of an aerosol, micropulverized powder or nebulized solution. For oral administration, they can be administered in the form of tablets, capsules, for example, in admixture with talc, starch, milk sugar or other inert ingredients, that is, pharmaceutically acceptable carriers, or in the form of aqueous solutions, suspensions, elixirs or aqueous alcoholic solutions, for example, in admixture with sugar or other sweetening agents, flavoring agents, colorants, thickeners and other conventional pharmaceutical excipients. For parenteral administration, they can be administered as solutions or suspension, for example, as an aqueous or peanut oil suspension using excipients and carriers conventional for this mode of administration. For administration as aerosols, they can be dissolved in a suitable pharmaceutically acceptable solvent, for example, ethyl alcohol or combinations of miscible solvents, and mixed with a pharmaceutically acceptable propellant. Such aerosol compositions are packaged for use in pressurized container fitted with an aerosol valve suitable for release of the pressurized composition. Preferably, the aerosol valve is a metered valve, that is one which on activation releases a predetermined effective dose of the aerosol composition. For topical use, they can conveniently be used in the form of salves, tinctures, creams, solutions, lotions, sprays, suspensions and the like. Salves and creams as well as solutions are preferred. These topical preparations can be prepared by mixing a compound of formula I as an active ingredient with one or more non-toxic, inert, solid or liquid carriers which are usual in such preparations and which are suitable for topical treatment.

The Examples which follow further illustrate the invention. All temperatures set forth in the specification and the Examples are in degrees Centigrade. Melting points were taken on a Thomas Hoover capillary melting point apparatus and are uncorrected. All compounds were characterized by proton magnetic resonance spectra taken on a Varian XL-200 or XL-400 spectrometer and electron impact or fast atom bombardment mass spectra taken on either VG ZAB-1F or VG 70E-HF mass spectrometers. Preparative high-pressure liquid chromatography (HPLC) was performed on silica gel Prep-Pak 500 cartridges using a Waters Associates Prep LC 500A. Extracts were dried over anhydrous magnesium sulfate unless otherwise noted.

EXAMPLE 1

N-(2-Methoxy-2-oxoethyl)-N-[3-(octadecyloxy)benzoyl]glycine methyl ester

A suspension of 1.0 g (2.56 mmol) of 3-(octadecyloxy)benzoic acid, which is a known compound, in 10 ml of thionyl chloride was stirred at reflux for 1.5 hours at which time most of the solid had dissolved. Anhydrous toluene (5 ml) was added and reflux was continued for 3 hours. The reaction mixture was concentrated at reduced pressure to yield a yellow solid. This acid chloride in 10 ml of anhydrous THF was added to an ice bath cooled solution of 0.52 g (3.2 mmol) of dimethyl iminodiacetate and 1.3 ml (9.2 mmol) of triethylamine in 40 ml of anhydrous THF. The reaction mixture was stirred at room temperature for 18 hours and then was concentrated at reduced pressure. The residue was extracted with ethyl acetate and the extract was washed with water, dried and concentrated. The residue was purified by chromatography on 80 g of silica gel using 20-50% ethyl acetate-hexane and recrystallization of the combined pure fractions from ether-hexane to give 0.78 g, mp 53°–55°, of N-(2-methoxy-2-oxoethyl)-N-[3-(octadecyloxy)benzoyl]glycine methyl ester.

Anal. Calcd for $C_{31}H_{51}NO_6$: C, 69.76; H, 9.63; N, 2.62. Found: C, 69.53; H, 9.84; N, 2.54.

EXAMPLE 2

N-(2-Methoxy-2-oxoethyl)-N-[3-(tetradecyloxy)benzoyl]glycine methyl ester

The conversion of 3-(tetradecyloxy)benzoic acid to the acid chloride followed by treatment with dimethyl iminodiacetate as in Example 1 gave N-(2-methoxy-2-oxoethyl)-N-[3-(tetradecyloxy)benzoyl]glycine methyl ester, mp <23°. The nmr and mass spectra were consistent with the structure.

EXAMPLE 3

N-(2-Methoxy-2-oxoethyl)-N-[3-(decyloxy)benzoyl]glycine methyl ester

The conversion of 3-(decyloxy)benzoic acid to the acid chloride followed by treatment with dimethyl iminodiacetate as in Example 1 gave N-(2-methoxy-2-oxoethyl)-N-[3-(decyloxy)benzoyl]glycine methyl ester as an oil. The nmr and mass spectra were consistent with the structure.

EXAMPLE 4

N-(Carboxymethyl)-N-[3-(octadecyloxy)benzoyl]glycine

A solution of 0.78 g (1.46 mmol) of N-(2-methoxy-2-oxoethyl)-N-[3-(octadecyloxy)benzoyl]glycine methyl ester and 7.0 ml (7 mmol) of 1N NaOH in 15 ml of methanol was stirred at reflux under argon for 2 hours. The solvent was removed at reduced pressure and the residue was acidified and the product was extracted with chloroform. The dried extract was concentrated to a solid which was recrystallized from ethyl acetate-hexane to give 0.60 g, mp 95°–99°, of N-(carboxymethyl)-N-[3-(octadecyloxy)benzoyl]glycine.

Anal. Calcd for $C_{29}H_{47}NO_6$: C, 68.88; H, 9.37; N, 2.77. Found: C, 68.74; H, 9.23; N, 2.65.

EXAMPLE 5

N-(Carboxymethyl)-N-[3-(tetradecyloxy)benzoyl]glycine

Sodium hydroxide hydrolysis of N-(2-methoxy-2-oxoethyl)-N-[3-(tetradecyloxy)benzoyl]glycine methyl ester as in Example 4 gave N-(carboxymethyl)-N-[3-(tetradecyloxy)benzoyl]glycine, mp 96°–99°.

Anal. Calcd for $C_{25}H_{39}NO_6$: C, 66.79; H, 8.74; N, 3.12. Found: C, 66.82; H, 8.75; N, 3.27.

EXAMPLE 6

N-(Carboxymethyl)-N-[3-(decyloxy)benzoyl]glycine

Sodium hydroxide hydrolysis of N-(2-methoxy-2-oxoethyl)-N-[3-(decyloxy)benzoyl]glycine methyl ester as in Example 4 gave N-(carboxymethyl)-N-[3-(decyloxy)benzoyl]glycine, mp 87°–90°.

Anal. Calcd for $C_{21}H_{31}NO_6$: C, 64.10; H, 7.94; N, 3.56. Found: C, 64.23; H, 7.97; N, 3.48.

EXAMPLE 7

N-(3-Aminobenzoyl)-N-(2-ethoxy-2-oxoethyl)glycine ethyl ester

To a solution of 2.5 g (12.9 mmol) of diethyl iminodiacetate and 4.5 ml (32.4 mmol) of triethylamine in 50 ml of methylene chloride stirred at room temperature was added 2.0 g (10.8 mmol) of 3-nitrobenzoyl chloride. The reaction mixture was stirred at room temperature for 18 hours, 50 ml of water was added and the organic layer was separated, dried and concentrated at reduced pressure to an oil. Purification by chromatography on 100 g of silica gel using 28% ethyl acetate-hexane-2% methylene chloride gave 3.3 g, mp 69°–72°, of N-(3-nitrobenzoyl)-N-(2-ethoxy-2-oxoethyl)glycine ethyl ester.

Anal. Calcd for $C_{15}H_{18}N_2O_7$: C, 53.25; H, 5.36; N, 8.28. Found: C, 53.21; H, 5.32; N, 8.12.

A mixture of 3.3 g of N-(3-nitrobenzoyl)-N-(2-ethoxy-2-oxoethyl) glycine ethyl ester and 0.5 g of 10% palladium on carbon in 40 ml THF and 40 ml ethyl acetate was stirred in a hydrogen atmosphere for 16 hours. The catalyst was removed by filtration and the filtrate was concentrated at reduced pressure to an oil which was purified by HPLC using 50% ethyl acetate-hexane to remove an impurity and ethyl acetate to elute 3.1 g of N-(3-aminobenzoyl)-N-(2-ethoxy-2-oxoethyl)glycine ethyl ester as an oil. The nmr and mass spectra were consistent with the structure.

EXAMPLE 8

N-(2-Ethoxy-2-oxoethyl)-N-[3-(1oxooctadecylamino)-benzoyl]glycine ethyl ester

To an ice bath cooled solution of 3.1 g (10.06 mmol) of N-(3-aminobenzoyl)-N-(2-ethoxy-2-oxoethyl)glycine ethyl ester and 2.6 ml (19 mmol) of triethylamine in 60 ml of methylene chloride was added dropwise 3.2 ml (9.6 mmol) of stearoyl chloride. The reaction mixture was stirred in the cold for 30 minutes and then at room temperature for 5 hours. The mixture was poured into water containing 1N HCl and the product was extracted with ethyl acetate. The dried extract was concentrated to a solid which was purified by chromatography on 70 g of silica gel using 35% ethyl acetate: 10% methylene chloride: 55% hexane and then recrystallization from ethyl acetate-hexane to give 4.5 g (78% yield, mp 76°-79°) of N-(2-ethoxy-2-oxoethyl)-N-[3-(1-oxooctadecylamino)benzoyl]glycine ethyl ester.

Anal. Calcd for $C_{33}H_{54}N_2O_6$: C, 68.96; H, 9.47; N, 4.87. Found: C, 69.07; H, 9.58; N, 4.88.

EXAMPLE 9

N-(Carboxymethyl)-N-[3-(1-oxooctadecylamino) benzoyl]glycine

A solution of 3.0 g (5.2 mmol) of N-(2-ethoxy-2-oxoethyl)-N-[3-(1-oxooctadecylamino)benzoyl]glycine ethyl ester and 25 ml (25 mmol) of 1N NaOH in 100 ml of methanol was stirred at reflux for 6 hours. The solvent was removed at reduced pressure, the residue was acidified and the precipitate was filtered and recrystallized from ethyl acetate-hexane to give 2.0 g (74% yield, mp 132°-142° ) of N-(carboxymethyl)-N-[3-(1-oxooctadecylamino)benzoyl]glycine.

Anal. Calcd for $C_{29}H_{46}N_2O_6$: C, 67.15; H, 8.94; N, 5.40. Found: C, 66.89; H, 8.96; N, 5.30.

EXAMPLE 10

N-[3,5-bis(Decyloxy)benzoyl]-N-(2-methoxy-2-oxoethyl)glycine methyl ester

To 4.0 g (9.2 mmol) of 3,5-bis(decyloxy)benzoic acid, which is a known compound, in 40 ml of anhydrous toluene stirred and cooled in an ice bath was added 1.6 ml (18.4 mmol) of oxalyl chloride. The mixture was stirred at room temperature for 3 hours and then was heated at 60° for 8 hours. The solvent was removed at reduced pressure to give the acid chloride as an oil. This was dissolved in 30 ml of methylene chloride and added dropwise to a solution of 1.85 g (11.5 mmol) dimethyl iminodiacetate and 2.6 ml (18.4 mmol) of triethylamine in 10 ml of methylene chloride. After stirring at room temperature for 16 hours, the reaction mixture was washed with NaHCO$_3$ solution, dried and concentrated to an oil. Purification by HPLC using 15% ethyl acetate-hexane gave 4.3 g (81% yield) of N-[3,5-bis(decyloxy)benzoyl]-N-(2-methoxy-2-oxoethyl)glycine methyl ester as an oil. The nmr and mass spectra were consistent with the structure.

EXAMPLE 11

N-(Carboxymethyl)-N-[3,5-bis(decyloxy)benzoyl]glycine

A solution of 3.3 g (5.7 mmol) of N-[3,5-bis(decyloxy)benzoyl]-N-(2-methoxy-2-oxoethyl)glycine methyl ester and 23 ml (23 mmol) of 1N NaOH in 250 ml of methanol was stirred at room temperature for 17 hours and then at reflux for 3 hours. The solvent was removed at reduced pressure, the residue was acidified and the product was extracted with ethyl acetate. The dried extract was concentrated to give 3.0 g, mp 81°-84°, of N-(carboxymethyl)-N-[3,5-bis(decyloxy) benzoyl]glycine.

Anal. Calcd for $C_{31}H_{51}NO_7$: C, 67.73; H, 9.35; N, 2.55. Found: C, 68.07; H, 9.28; N, 2.61.

EXAMPLE 12

N-[3,5-bis(Tetradecyloxy)benzoyl]-N-(2-methoxy-2-oxoethyl)glycine methyl ester

The reaction of 3,5-bis(tetradecyloxy)benzoyl chloride with dimethyl iminodiacetate as in Example 10 gave N-[3,5-bis (tetradecyloxy)benzoyl]-N-(2-methoxy-2-oxoethyl)glycine methyl ester as an oil. The nmr and mass spectra were consistent with the structure.

EXAMPLE 13

N-(Carboxymethyl)-N-[3,5-bis(tetradecyloxy)benzoyl]glycine

Sodium hydroxide hydrolysis of N-[3,5-bis(tetradecyloxy)benzoyl]-N-(2-methoxy-2-oxoethyl)glycine methyl ester as in Example 11 gave N-(carboxymethyl)-N-[3,5-bis(tetradecyloxy)benzoyl]glycine, mp 88°-90°.

Anal. Calcd for $C_{39}H_{67}NO_7$: C, 70.76H, 10.20; N, 2.12. Found: C, 70.93; H, 10.44; N, 2.14.

EXAMPLE 14

3-Hydroxy-5-(octadecyloxy)benzoic acid phenylmethyl ester

A mixture of 30 g (0.123 mol) of 3,5-dihydroxybenzoic acid phenylmethyl ester, 40.9 g (0.123 mol) of 1-bromooctadecane, 17 g (0.123 mol) of anhydrous potassium carbonate in 500 ml of acetone and 10 ml of DMF was stirred at reflux for 25 hours. The reaction mixture was filtered and the filtrate was concentrated at reduced pressure to a solid. The residue was treated with water and the product was extracted with methylene chloride. The dried extract was concentrated at reduced pressure to a solid which was purified by HPLC using 1% ethyl acetate-methylene chloride to give 22 g (36% yield, mp 72°-75°) of 3-hydroxy-5-(octadecyloxy)benzoic acid phenylmethyl ester. The structure was confirmed by nmr and mass spectra.

EXAMPLE 15

3-(Octadecyloxy)-5-(3-phenoxypropoxy)benzoic acid phenylmethyl ester

A mixture of 12 g (0.024 mol) of 3-hydroxy-5-(octadecyloxy)benzoic acid phenylmethyl ester, 6 ml (0.038 mol) of 3-phenoxypropyl bromide, 3.6 g (0.024 mol) of sodium iodide and 10 g (0.072 mol) of potassium carbonate in 400 ml of acetone and 80 ml of DMF was stirred at reflux for 46 hours. The reaction mixture was filtered and the filtrate was concentrated to dryness at reduced pressure. Water was added to the residue and the product was extracted with ethyl acetate. The dried extract was concentrated at reduced pressure to an oil which was purified by HPLC using 5% ethyl acetate-hexane. The pure fractions were combined, triturated with hexane and filtered to give 14.6 g (96% yield, mp 46°-47°) of 3-(octadecyloxy)-5-(3-phenoxypropoxy)-benzoic acid phenylmethyl ester. The structure was confirmed by nmr and mass spectra.

EXAMPLE 16

3-(Octadecyloxy)-5-(3-phenoxypropoxy)benzoic acid

A mixture of 14.6 g of 3-(octadecyloxy)-5-(3-phenoxypropoxy) benzoic acid phenylmethyl ester and 3 g of 10% palladium on carbon in 200 ml THF and 20 ml ethyl acetate was shaken in a hydrogen atmosphere at room temperature for 2 hours. The catalyst was removed by filtration and the filtrate was concentrated to a solid which was recrystallized from ether-hexane to give 11.8 g (95% yield, mp 79°-81°) of 3-(octadecyloxy)-5-(3-phenoxypropoxy)benzoic acid.

Anal. Calcd for $C_{34}H_{52}O_5$: C, 75.52; H, 9.69. Found: C, 75.09; H, 9.80.

EXAMPLE 17

N-(2-Ethoxy-2-oxoethyl)-N-[3-[3-(phenoxy)propoxy]-5-(octadecyloxy)benzoyl]glycine ether ester A solution of 1.0 g (1.85 mmol) of 3-(octadecyloxy)-5-(3-phenoxypropoxy)benzoic acid in 10 ml of thionyl chloride and 4 ml of toluene was stirred at reflux for 4.5 hours. The mixture was concentrated at reduced pressure, the residual acid chloride was dissolved in 10 ml of anhydrous THF and added dropwise to a solution of 0.44 g (2.3 mmol) of diethyl iminodiacetate and 0.8 ml (5.8 mmol) of triethylamine in 20 ml of THF with stirring. The reaction mixture was stirred at room temperature for 16 hours and then was concentrated at reduced pressure to yield an oil. Purification by HPLC using 20% ethyl acetate-hexane to give 1.2 g of N-(2-ethoxy-2-oxoethyl)-N-[3-[3-(phenoxy)propoxyl]-5-(octadecyloxy)benzoyl] glycine ethyl ester as an oil.

Anal. Calcd for $C_{42}H_{61}NO_8$: C, 71.26; H, 8.69; N, 1.98. Found: C, 70.73; H, 9.15; N, 1.88.

EXAMPLE 18

N-(Carboxymethyl)-N-[3-[3-(phenoxy)propoxy]-5-(octadecyloxy)benzoyl]glycine

Sodium hydroxide hydrolysis of N-(2-ethoxy-2-oxoethyl)-N-[3-[3-(phenoxy)propoxy]-5-(octadecyloxy)benzoyl]glycine ethyl ester as in Example 11 gave N-(carboxymethyl)-N-[3-[3-(phenoxy)propoxy]-5-(octadecyloxy)benzoyl]glycine, mp 86°-90°.

Anal. Calcd for $C_{38}H_{57}NO_8$: C, 69.59; H, 8.76; N, 2.14. Found: C, 69.37; H, 8.78; N, 2.16.

EXAMPLE 19

N-(2-Ethoxy-2-oxoethyl)-N-[3-[3-(4-methoxyphenoxy)propoxy]-5-(octadecyloxy)benzoyl]glycine ethyl ester 3-[3-(4-Methoxyphenoxy)propoxy]-5-(octadecyloxy)benzoic acid was converted to the acid chloride which was treated with diethyl iminodiacetate using the procedure of Example 17 to give N-(2-ethoxy-2-oxoethyl)-N-[3-[3-(4-methoxyphenoxy)propoxy]-5-(octadecyloxy)benzoyl]glycine ethyl ester as an oil which exhibited nmr and mass spectra consistent with the structure.

EXAMPLE 20

N-(Carboxymethyl)-N-[3-[3-(4-(methoxyphenoxy)-propoxy]-5(octadecyloxy)benzoyl]glycine Sodium hydroxide hydrolysis of N-(2-ethoxy-2-oxoethyl)-N-[3-[3-(4-methoxyphenoxy)propoxy]-5-(octadecyloxy)benzoyl]glycine ethyl ester as in Example 11 gave N-(carboxymethyl)-N-[3-[3-(4-methoxyphenoxy)propoxy]-5-(octadecyloxy)benzoyl]glycine which gave nmr and mass spectra consistent with the structure.

EXAMPLE 21

N-(2-Ethoxy-2-oxoethyl)-N-[3-[3-(3-nitrophenoxy)-propoxy]-5-(octadecyloxy)benzoyl]glycine ethyl ester A solution of 4.0 g (6.83 mmol) of 3-[3-(3-nitrophenoxy)propoxy]-5-(octadecyloxy)benzoic acid in 65 ml of thionyl chloride was stirred at reflux for 2.5 hours. The excess thionyl chloride was removed at reduced pressure and the residual solid acid chloride was dissolved in 75 ml of methylene chloride and added dropwise to a stirred, ice bath cooled solution of 1.5 ml of diethyl iminodiacetate (8.5 mmol) and 1.9 ml (13.7 mmol) of triethylamine in 25 ml of methylene chloride. The reaction mixture was stirred in the cooling bath for 30 minutes, at room temperature for 20 hours and then was washed with $NaHCO_3$ solution. The dried organic layer was concentrated at reduced pressure to an oil which was purified by HPLC using 25% ethyl acetate-hexane to give 4.32 g (84% yield) of N-(2-ethoxy-2-oxoethyl)-N-[3-[3-(3-nitrophenoxy)propoxy]-5-(octadecyloxy)benzoyl]glycine ethyl ester as an oil. The structure was confirmed by the nmr and mass spectra.

EXAMPLE 22

N-(Carboxymethyl)-N-[3-[3-(3-nitrophenoxy)propoxy]-5-(octadecyloxy)benzoyl]glycine A solution of 4.32 g (5.71 mmol) of N-(2-ethoxy-2-oxoethyl)-N-[3-[3-(3-nitrophenoxy)propoxy]-5-(octadecyloxy)benzoyl]glycine ethyl ester and 3.8 ml (22.8 mmol) of 6N NaOH in 125 ml of methanol was stirred at reflux under argon for 2.5 hours. The solvent was removed at reduced pressure and the residue was acidified. The product was extracted with ethyl acetate and the dried extract was concentrated to a yellow foam which was crystallized from methanol-water to give 3.74 g (94% yield, mp 86°-88° ) of N-(carboxymethyl)-N-3-[3-(3-nitrophenoxy)propoxy]-5-(octadecyloxy)benzoyl]glycine.

Anal. Calcd for $C_{38}H_{56}N_2O_{10}$: C, 65.12; H, 8.05; N, 4.00. Found: C, 64.90; H, 8.03; N, 3.89.

EXAMPLE 23

N-(Carboxymethyl)-N-[3-[3-(3-aminophenoxy)propoxy]-5-(octadecyloxy)benzoyl]glycine A mixture of 0.50 g of N-(carboxymethyl)-N-3-[3-(3-nitrophenoxy)propoxy]-5-(octadecyloxy)benzoyl]glycine and 0.2 g of 10% palladium on carbon in 40 ml of THF was stirred under a hydrogen atmosphere at room temperature for 3 hours when uptake ceased. The catalyst was removed by filtration and the filtrate was concentrated to a solid which was recrystallized three times from ether-hexane to give 0.20 g (42% yield, mp 100°-104° ) of N-(carboxymethyl)-N-[3-[3-(3-aminophenoxy)propoxy]-5-(octadecyloxy)benzoyl]glycine.

Anal. Calcd for $C_{38}H_{58}N_2O_8 \cdot .5:4 \, H_2O$: C, 66.60; H, 8.77; N, 4.09; $H_2O$, 2.10. Found: C, 66.92; H, 8.73; N, 3.90; $H_2O$, 2.47.

EXAMPLE 24

N-(2-Ethoxy-2-oxoethyl)-N-[3-[2-(2-naphthyloxy) ethyloxy]-5-(octadecyloxy)]benzoyl]glycine ethyl ester A solution of 1.9 g (3.3 mmol) of 3-[2-(2-naphthalenyloxy) ethoxy]-5-(octadecyloxy)benzoic acid and 1.5 ml (16.5 mmol) of oxalyl chloride in 50 ml of anhydrous toluene, 50 ml of methylene chloride and 2 drops of anhydrous DMF was stirred at reflux for 2 hours. The solvents were removed at reduced pressure and the acid chloride was dissolved in 100 ml of methylene chloride and added dropwise to a stirred, ice bath cooled solution of 0.75 g (3.96 mmol) of diethyl iminodiacetate and 1.4 ml (10 mmol) of triethylamine in 20 ml of methylene chloride. The mixture was stirred at room temperature for 17 hours. The usual workup and purification by HPLC using 25% ethyl acetate-hexane gave 2.4 g (97% yield) of N-(2-ethoxy-2-oxoethyl)-N-[3-[2-(2-naphthyloxy)ethyloxy]-5-(octadecyloxy)]benzoyl]glycine ethyl ester as an oil.

EXAMPLE 25

N-(Carboxymethyl)-N-[3-[2-(2-naphthyloxy)ethyloxy]-5-(octadecyloxy)]benzoyl]glycine Sodium hydroxide hydrolysis of N-(2-ethoxy-2-oxoethyl)-N-[3-[2-(2-naphthyloxy)ethyloxy]-5-(octadecyloxy)]benzoyl]glycine ethyl ester as in Example 11 gave N-(carboxymethyl)-N-[3-[2-(2-naphthyloxy)ethyloxy]-5-(octadecyloxy)]benzoyl]glycine (46% yield) as an oil.

Anal. Calcd for $C_{41}H_{57}NO_8$: C, 71.17; H, 8.30; N, 2.02. Found: C, 71.23; H, 8.39; N, 1.99.

EXAMPLE 26

5-Hydroxy-1,3-benzenedicarboxylic acid dimethyl ester

A mixture of 10 g of 3-hydroxybenzene-1,3-dicarboxylic acid and 1 ml of concentrated sulfuric acid in 100 ml of methanol was stirred at reflux for 16 hours. The solvent was removed at reduced pressure and water was added to the residue. The solid was filtered and dried to give 11.3 g, mp 155°–157°, of 5-hydroxy-1,3-benzenedicarboxylic acid dimethyl ester. The structure was confirmed by the nmr spectrum.

EXAMPLE 27

5-(Octadecyloxy)-1,3-benzenedicarboxylic acid dimethyl ester

A mixture of 3.0 g (14.3 mmol) of 5-hydroxy-1,3-benzenedicarboxylic acid dimethyl ester, 5.2 g (15.7 mmol) of 1-bromooctadecane and 5.8 g (42 mmol) of potassium carbonate in 120 ml of acetone and 30 ml of DMF was stirred at reflux for 16 hours. The reaction mixture was concentrated at reduced pressure and water was added to the residue. The precipitate was removed by filtration and purified by recrystallization from methylene chloride-methanol to give 6.35 g, mp 54°–55°, of 5-(octadecyloxy)-1,3-benzenedicarboxylic acid dimethyl ester. The structure was confirmed by nmr and mass spectra.

EXAMPLE 28

5-(Octadecyloxy)-1,3-benzenedicarboxylic acid monomethyl ester

To a solution of 6.35 g (13.7 mmol) of 5-(octadecyloxy)-1,3-benzenedicarboxylic acid dimethyl ester in 275 ml of dioxane and 275 ml of methanol was added 13.7 ml (13.7 mmol) of 1N NaOH. The reaction mixture was stirred at room temperature for 45 minutes and then was heated briefly to dissolve the precipitate. After stirring at room temperature for 16 hours, the reaction mixture was heated to reflux for 30 minutes. The solvent was removed at reduced pressure and the residue was acidified. The precipitate was filtered and recrystallized from ethyl acetate-hexane to give 2.08 g, mp 81°–83°, of 5-(octadecyloxy)-1,3-benzenedicarboxylic acid monomethyl ester.

Anal. Calcd for $C_{27}H_{44}O_5$: C, 72.28; H, 9.89. Found: C, 72.13; H, 9.86.

EXAMPLE 29

N-(2-Ethoxy-2-oxoethyl)-N-[3-methoxycarbonyl-5-(octadecyloxy)benzoyl]glycine ethyl ester Conversion of 5-(octadecyloxy-1,3-benzenedicarboxylic acid monomethyl ester to the acid chloride with thionyl chloride followed by treatment with diethyl iminodiacetate as described earlier gave N-(2-ethoxy-2-oxoethyl)-N-[3-methoxycarbonyl-5-(octadecyloxy) benzoyl]glycine ethyl ester, mp 57°–60°.

Anal. Calcd for $C_{33}H_{53}NO_8$: C, 66.98; H, 9.03; N, 2.37. found: C, 67.13; H, 9.05; N, 2.36.

EXAMPLE 30

N-(Carboxymethyl)-N-[3-carboxy-5-(octadecyloxy) benzoyl]glycine

Sodium hydroxide hydrolysis of N-(2-ethoxy-2-oxoethyl)-N-[3-methoxycarbonyl-5-(octadecyloxy)benzoyl]glycine ethyl ester as in Example 11 gave N-(carboxymethyl)-N-[3-carboxy-5-(octadecyloxy) benzoyl]glycine, mp 108°–112°. The nmr and mass spectra were compatible with the structure.

EXAMPLE 31

3-(2-Methoxy-2-oxoethoxy)-5-(octadecyloxy)benzoic acid

A mixture of 5.0 g (10 mmol) of 3-hydroxy-5-(octadecyloxy) benzoic acid phenylmethyl ester (from Example 14), 1.87 ml (20 mmol) of methyl bromoacetate, 3.5 g (25 mmol) of potassium carbonate and 1.5 g (10 mmol) of sodium iodide in 100 ml of acetone and 20 ml of anhydrous DMF was stirred at reflux under argon for 24 hours. The solvents were removed at reduced pressure and the residue was extracted with ethyl acetate. The dried extract was concentrated to an oil and purified by HPLC using 15% ethyl acetate-hexane to give 4.4 g, mp 55°–58°, of 3-(2-methoxy-2-oxoethoxy)-5-(octadecyloxy)benzoic acid phenylmethyl ester.

Anal. Calcd for $C_{35}H_{52}O_6$: C, 73.91; H, 9.21. Found: C, 74.00; H, 9.04.

A mixture of 5.0 g of 3-(2-methoxy-2-oxoethoxy)-5-(octadecyloxy) benzoic acid phenylmethyl ester and 0.6 g of 10% palladium on carbon in 50 ml of THF and 30 ml of ethyl acetate was stirred under a hydrogen atmosphere for 2.5 hours when uptake ceased. The catalyst was removed by filtration and the filtrate was concentrated to a solid which was recrystallized from ethyl acetate-hexane to give 3.5 g, mp 95°–97°, of 3-(2-methoxy-2-oxoethoxy)-5-(octadecyloxy) benzoic acid.

Anal. Calcd for $C_{28}H_{46}O_6$: C, 70.26; H, 9.69. Found: C, 70.00; H, 9.73.

EXAMPLE 32

N-[3-(2-Methoxy-2-oxoethoxy)-5(octadecyloxy)benzoyl]-N-(2-methoxy-2-oxoethyl)glycine methyl ester A solution of 1.668 g (3.5 mmol) of 3-(2-methoxy-2-oxoethoxy)-5-(octadecyloxy)benzoic acid in 30 ml of thionyl chloride was stirred at reflux for 3 hours. The excess thionyl chloride was removed at reduced pressure and the resultant acid chloride was dissolved in 20 ml of methylene chloride-10 ml of anhydrous THF and was added dropwise with stirring to an ice cooled solution of 0.7 ml (4.3 mmol) of dimethyl iminodiacetate and 1 ml (7 mmol) of triethylamine in 20 ml of methylene chloride. The reaction mixture was left at room temperature for 2 days and concentrated at reduced pressure. The residue was extracted with ethyl acetate and the extract was washed successively with 1N HCl and with NaHCO$_3$ solution, dried and concentrated at reduced pressure to a solid which was recrystallized from methanol-water to give 1.73 g, mp 53°–55°, of N-[3-(2-methoxy-2-oxoethoxy)-5-(octadecyloxy)benzoyl]-N-(2-methoxy-2-oxoethyl)glycine methyl ester.

Anal. Calcd for C$_{34}$H$_{55}$NO$_9$: C, 65.67; H, 8.92; N, 2.25. Found: C, 65.26; H, 8.85; N, 2.13.

EXAMPLE 33

N-(Carboxymethyl)-N-[3-(carboxymethoxy)-5-(octadecyloxy)benzoyl]glycine

A solution of 1.7 g (3.5 mmol) of N-[3-(2-methoxy-2-oxoethoxy)-5-(octadecyloxy)benzoyl]-N-(2-methoxy-2-oxoethyl)glycine methyl ester and 2.8 ml (16.8 mmol) of 6N NaOH in 125 of methanol and 50 ml of dioxane was left at room temperature for 17 hours. The reaction mixture was then stirred at reflux for 5 hours and the solvents were removed at reduced pressure. The residue was shaken well with 1N HCl to acidify and the solid was removed by filtration. Recrystallization from methanol-water gave 1.06 g, mp 134°–136°, of N-(carboxymethyl)-N-[3-(carboxymethoxy)-5-(octadecyloxy)benzoyl]glycine. The nmr and mass spectra were consistent with the structure.

EXAMPLE 34

N-(2-Ethoxy-2-oxoethyl)N-[3,5-bis[(11-methoxy-11-oxoundecyl)oxy]benzoyl]glycine ethyl ester Conversion of 3,5-bis[(11-methoxy-11-oxoundecyl)oxy]benzoic acid to the acid chloride with thionyl chloride followed by treatment with diethyl iminodiacetate as in Example 21 gave N-(2-ethoxy-2-oxoethyl)-N-[3,5-bis[(11-methoxy-11-oxoundecyl)oxy]-benzoyl]glycine ethyl ester as an oil after chromatography on 125 g of silica gel using 20% ethyl acetate-hexane.

Anal. Calcd for C$_{39}$H$_{63}$NO$_{11}$: C, 64.89; H, 8.80; N, 1.94. Found: C, 64.72; H, 8.82; N, 1.85.

EXAMPLE 35

N-(Carboxymethyl)-N-[3,5-bis[(10-carboxydecyl)oxy]benzoyl]glycine

Sodium hydroxide hydrolysis of N-(2-ethoxy-2-oxoethyl)-N-[3,5-bis[(11-methoxy-11-oxoundecyl)oxy]benzoyl]glycine ethyl ester gave N-(carboxymethyl)-N-[3,5-bis[(10-carboxydecyl)oxy]benzoyl]glycine, mp 134°–140°.

Anal. Calcd for C$_{33}$H$_{51}$NO$_{11}$.0.5 H$_2$O: C, 61.28; H, 8.10; N, 2.16; H$_2$O, 1.39. Found: C, 61.09; H, 7.89; N, 1.99; H$_2$O, 1.29.

EXAMPLE 36

3-(Octadecyloxy)-5-(phenylmethoxy)benzoic acid

A mixture of 3.0 g (7.1 mmol) of 3-hydroxy-5-(octadecyloxy) benzoic acid methyl ester, 0.93 ml (7.85 mmol) of benzyl bromide and 2.0 g (14.5 mmol) of potassium carbonate in 50 ml of DMF was stirred at 85° for 50 hours. The solvent was removed at reduced pressure and the residue was extracted with methylene chloride. The extract was concentrated and recrystallized from methylene chloride-methanol to give 3.24 g (89% yield, mp 62°–64°) of 3-(octadecyloxy)-5-(phenylmethoxy)benzoic acid methyl ester. A solution of 3.24 g (6.3 mmol) of 3-(octadecyloxy)-5-(phenylmethoxy) benzoic acid methyl ester and 3 ml (18 mmol) of 6N NaOH in 100 ml of methanol and 25 ml of dioxane was stirred at reflux for 3.5 hours. The solvents were removed at reduced pressure and the residue was acidified and extracted with ethyl acetate. The dried extract was concentrated to a solid which was recrystallized from methylene chloride-hexane to give 2.77 g (88% yield, mp 101°–103°) of 3-(octadecyloxy)-5-(phenylmethoxy)-benzoic acid.

EXAMPLE 37

N-(2-Methoxy-2-oxoethyl)-N-[3-(octadecyloxy)-5-(phenylmethoxy)benzoyl]glycine methyl ester Conversion of 3-(octadecyloxy)-5-(phenylmethoxy)benzoic acid to the acid chloride with thionyl chloride followed by treatment with dimethyl iminodiacetate gave N-(2-methoxy-2-oxoethyl)-N-[3-(octadecyloxy)-5-(phenylmethoxy)benzoyl]glycine methyl ester as an oil after chromatography on 50 g of silica gel using 25% ethyl acetate-hexane. The structure was confirmed by the nmr spectrum.

EXAMPLE 38

N-(Carboxymethyl)-N-[3-(octadecyloxy)-5-(phenylmethoxy)benzoyl]glycine

Sodium hydroxide hydrolysis of N-(2-methoxy-2-oxoethyl)-N-[3-(octadecyloxy)-5-(phenylmethoxy)benzoyl]glycine methyl ester gave N-(carboxymethyl)-N-[3-(octadecyloxy)-5-(phenylmethoxy)benzoyl]glycine, mp 93°–95°.

Anal. Calcd for C$_{36}$H$_{53}$NO$_7$: C, 70.67; H, 8.73; N, 2.29. Found: C, 70.59; H, 8.80; N, 2.35.

EXAMPLE 39

N-(Carboxymethyl)-N-[3-hydroxy-5-(octadecyloxy)benzoyl]glycine

A mixture of 0.30 g of N-(carboxymethyl)-N-[3-(octadecyloxy)-5-(phenylmethoxy)benzoyl]glycine and 0.1 g of 10% palladium on carbon in 25 ml of THF was stirred in a hydrogen atmosphere for 2 hours. The usual workup followed by recrystallization from ether-hexane gave N-(carboxymethyl)-N-[3-hydroxy-5-(octadecyloxy)benzoyl]glycine, mp 160°–164°.

Anal. Calcd for C$_{29}$H$_{47}$NO$_7$: C, 66.77; H, 9.08; N, 2.68. Found: C, 66.58; H,. 9.02; N, 2.67.

EXAMPLE 40

3-Nitro-5-(octadecyloxy)benzoic acid methyl ester

A mixture of 1.7 g (8.6 mmol) of 3-hydroxy-5-nitrobenzoic acid methyl ester [prepared as described by D. J. Abraham, D. M. Gazze, P. E. Kennedy and M. Mokotoff, J. Med. Chem. 27, 1549 (1984)], 3.2 g (9.5 mmol) of 1-bromooctadecane and 1.8 g (12.9 mmol) of potassium carbonate in 35 ml of anhydrous DMF was stirred and heated at 75° for 25 hours. After cooling, 150 ml of methylene chloride was added and the insoluble salts were removed by filtration. The filtrate was concentrated at reduced pressure to a solid which was purified by HPLC using 30% methylene chloridehexane to give 3.57 g (92% yield, mp 64°-66°) of 3-nitro-5-(octadecyloxy)benzoic acid methyl ester.

Anal. Calcd for $C_{26}H_{43}NO_5$: C, 69.45; H, 9.64; N, 3.12. Found: C, 69.39; H, 9.66; N, 3.04.

EXAMPLE 41

3-Nitro-5-(octadecyloxy)benzoic acid

A solution of 4.5 g of 3-nitro-5-(octadecyloxy)benzoic acid methyl ester and 4 ml of 6N NaOH in 200 ml of methanol and 50 ml of dioxane was stirred at reflux for 2.5 hours. The solvents were removed at reduced pressure and the residue was acidified with 1N HCl. The solid was filtered and recrystallized from methanol-water to give 2.7 g (62% yield, mp 101°-103°) of 3-nitro-5-(octadecyloxy) benzoic acid.

Anal. Calcd for $C_{25}H_{41}NO_5$: C, 68.93; H, 9.49; N, 3.22. Found: C, 67.94; H, 9.55; N, 3.02.

EXAMPLE 42

N-(2-Methoxy-2-oxoethyl)-N-[3-nitro-5-(octadecyloxy) benzoyl]glycine methyl ester Conversion of 3-nitro-5-(octadecyloxy)benzoic acid to the acid chloride with thionyl chloride followed by treatment with dimethyl iminodiacetate gave a 79% yield of N-(2-methoxy-2-oxoethyl)-N-[3-nitro-5-(octadecyloxy)benzoyl]glycine methyl ester as an oil after chromatography on silica gel using 25% ethyl acetate-hexane. The nmr spectrum was consistent with the structure.

EXAMPLE 43

N-(Carboxymethyl)-N-[3-nitro-5-(octadecyloxy) benzoyl]glycine

Sodium hydroxide hydrolysis of N-(2-methoxy-2-oxoethyl)-N-[3-nitro-5-(octadecyloxy)benzoyl]glycine methyl ester gave a 92% yield of N-(carboxymethyl)-N-[3-nitro-5-(octadecyloxy)benzoyl]glycine, mp 110°-112°.

Anal. Calcd for $C_{29}H_{46}N_2O_8$: C, 63.25; H, 8.42; N, 5.09. Found: C, 63.12; H, 8.54; N, 5.08.

EXAMPLE 44

N-(Carboxymethyl)-N-[3-amino-5-(octadecyloxy)benzoyl]glycine

Catalytic hydrogenation of N-(carboxymethyl)-N-[3-nitro-5-(octadecyloxy)benzoyl]glycine under the usual conditions gave N-(carboxymethyl)-N-[3-amino-5-(octadecyloxy)benzoyl]glycine mp 108°-120°.

Anal. Calcd for $C_{29}H_{48}N_2O_6$: C, 66.89; H, 9.29; N, 5.38. Found: C, 66.77; H, 9.32; N, 5.11.

EXAMPLE 45

3-[2-[2-(2-Ethoxyethoxy)ethoxy]ethoxy]-5-(octadecyloxy)benzoic acid phenylmethyl ester A mixture of 2 g (4 mmol) of 3-hydroxy-5-(octadecyloxy)benzoic acid phenylmethyl ester, 3.65 g (15.8 mmol) of 2-[2-(2-ethoxyethoxy)ethoxy]ethyl bromide, 1.2 g (8 mmol) of sodium iodide and 2.2 g (16 mmol) of potassium carbonate in 60 ml of acetone and 30 ml of DMF was stirred at reflux for 40 hours. The usual workup followed by chromatography of the crude product on 200 g of silica gel using 40% ethyl acetate-hexane gave 1.76 g of 3-[2-[2-(2-ethoxyethoxy)ethoxy]ethoxy]-5-(octadecyloxy)benzoic acid phenylmethyl ester as an oil. The nmr and mass spectra were compatible with the structure.

EXAMPLE 46

3-[2-[2-(2-Ethoxyethoxy)ethoxy]ethoxy]-5-(octadecyloxy)benzoic acid

A solution of 1.76 g (2.7 mmol) of 3-[2-[2-(2-ethoxyethoxy)ethoxy]ethoxy]-5-(octadecyloxy)benzoic acid phenylmethyl ester and 2.3 ml (13.8 mmol) of 6N NaOH in 50 ml of methanol and 10 ml of dioxane was kept at room temperature for 2.5 hours and then was stirred at reflux for 45 minutes. The solvents were removed at reduced pressure, the residue was acidified and the product was extracted with ethyl acetate. The dried extract was concentrated to a solid which was recrystallized from methanol-water to give 1.3 g, mp 38°-40°, of 3-[2-[2-(2-ethoxyethoxy)ethoxy]ethoxy]-5-(octadecyloxy) benzoic acid.

Anal. Calcd for $C_{33}H_{58}O_7$: C, 69.93; H, 10.31. Found: C, 69.62; H, 10.15.

EXAMPLE 47

N-(2-Ethoxy-2-oxoethyl)-N-[3-[2-[2-(2-ethoxyethoxy)ethoxy]ethoxy]-(5-octadecyloxy)benzoyl]glycine ethyl ester A solution of 1.0 g (1.76 mmol) of 3-[2-[2-(2-ethoxyethoxy) ethoxy]ethoxy]-5-(octadecyloxy)benzoic acid in 10 ml of thionyl chloride and 5 ml of toluene was stirred at reflux for 7 hours. The reaction mixture was concentrated at reduced pressure and the residual acid chloride was dissolved in 20 ml of anhydrous THF and added to a stirred mixture of 0.42 g (2.2 mmol) of diethyl iminodiacetate and 0.75 ml (5.3 mmol) of triethylamine in 5 ml of THF. The reaction mixture was stirred at room temperature for 16 hours and was then concentrated at reduced pressure. The residue was extracted with ethyl acetate and the extract was washed with water, dried and concentrated to an oil. Purification by chromatography on 30 g of silica gel (230-400 mesh) using 40% ethyl acetate-hexane gave 1.1 g (85% yield) of N-(2-ethoxy-2-oxoethyl)-N-[3-[2-[2-(2-ethoxyethoxy)ethoxy]ethoxy]-(5-octadecyloxy)benzoyl]glycine ethyl ester as an oil. The structure was confirmed by the nmr and mass spectra.

EXAMPLE 48

N-(Carboxymethyl)-N-[3-[2-[2-(2-ethoxyethoxy) ethoxy]ethoxy]-(5-octadecyloxy)benzoyl]glycine A solution of 1.0 g (1.36 mmol) of N-(2-ethoxy-2-oxoethyl)-N-[3-[2-[2-(2-ethoxyethoxy)ethoxy]ethoxy]-(5-octadecyloxy)benzoyl]glycine ethyl ester and 1.1 ml (6.6 mmol) of 6N NaOH in 25 ml of methanol was stirred at room temperature for 4 hours. The solvent was removed at reduced pressure, the residue was acidified and the product was extracted with ethyl acetate. The dried extract was concentrated to an oil which was purified by chromatography on 30 g of silica gel (230-400 mesh) using 25% methanol-chloroform to give 0.66 g (71% yield) of N-(carboxymethyl)-N-[3-[2-[2-(2-ethoxyethoxy)ethoxy]ethoxy]-(5-octadecyloxy)- benzoyl]glycine as an oil. The structure was confirmed by nmr and mass spectra.

Anal. Calcd for $C_{37}H_{63}NO_{10}$ .1:2 $H_2O$: C, 61.90; H, 9.41; N, 1.95; $H_2O$, 5.00. Found: C, 61.73; H, 9.14; N, 1.87; $H_2O$, 3.76.

EXAMPLE 49

3,4-bis(Tetradecyloxy)benzoic acid

A mixture of 1.0 g (6.6 mmol) of 3,4-dihydroxybenzoic acid methyl ester, 4.1 ml (14 mmol) of 1-bromotetradecane and 2.5 g (17.9 mmol) of potassium carbonate in 50 ml of DMF was stirred and heated at 100° for 65 hours. The solvent was removed using high vacuum, water was added to the residue and the product was extracted with ethyl acetate. The dried extract was concentrated to a solid which was recrystallized from methanol-water to give 1.1 g (30% yield, mp 49°–50°) of 3,4-bis(tetradecyloxy)benzoic acid methyl ester.

A solution of 3,4-bis(tetradecyloxy)benzoic acid methyl ester (1.1 g, 2.0 mmol) and 1.6 ml (9.6 mmol) of 6N NaOH in 40 ml of methanol and 20 ml of dioxane was stirred at reflux for 17 hours. The solvents were removed at reduced pressure, the residue was acidified and the solid was filtered and recrystallized from methanol-THF-water to give 0.8 g (73% yield, mp 112°–113°) of 3,4-bis(tetradecyloxy)benzoic acid.

Anal. Calcd for $C_{35}H_{62}O_4$: C, 76.87; H, 11.43. Found: C, 76.64; H, 11.44.

EXAMPLE 50

N-(2-Methoxy-2-oxoethyl)-N-[3,4-bis(tetradecyloxy)-benzoyl]glycine methyl ester

A solution of 0.8 g (1.46 mmol) of 3,4-bis(tetradecyloxy)benzoic acid and 20 ml of thionyl chloride was stirred at reflux for 3 hours. The excess thionyl chloride was removed at reduced pressure and the resultant acid chloride was dissolved in 10 ml of methylene chloride and 10 ml of anhydrous THF. This solution was added dropwise to a stirred, ice cooled mixture of 0.3 ml (1.86 mmol) of dimethyl iminodiacetate and 0.41 ml (2.9 mmol) of triethylamine in 10 ml of anhydrous methylene chloride. The cooling bath was removed after 30 minutes and the mixture was left at room temperature for 18 hours. The solvents were removed at reduced pressure and the residue was extracted with ethyl acetate. The extract was washed successively with 1N HCl, with NaHCO₃ solution, dried and concentrated. Crystallization from ethyl acetate-hexane gave 0.905 g (90% yield, mp 70°–71°) of N-(2-methoxy-2-oxoethyl)-N-[3,4-bis(tetradecyloxy)benzoyl]glycine methyl ester.

Anal. Calcd for $C_{41}H_{71}NO_7$: C, 71.37; H, 10.37; N, 2.03. Found: C, 71.21; H, 10.09; N, 1.81.

EXAMPLE 51

N-(Carboxymethyl)-N-[3,4-bis(tetradecyloxy)benzoyl]glycine

A solution of 0.90 g (1.3 mmol) of N-(2-methoxy-2-oxoethyl)-N-[3,4-bis(tetradecyloxy)benzoyl]glycine methyl ester and 1.0 ml (6 mmol) of 6N NaOH in 80 ml of methanol and 35 ml of dioxane was stirred at reflux for 6 hours. The solvents were removed at reduced pressure, the residue was acidified and the product was removed by filtration. Recrystallization from ethyl acetate-hexane gave 0.51 g (59% yield, mp 84°–87°) of N-(carboxymethyl)-N-[3,4-bis(tetradecyloxy)benzoyl]glycine.

Anal. Calcd for $C_{39}H_{67}NO_7$: C, 70.76; H, 10.20; N, 2.12. Found: C, 70.80; H, 10.12; N, 2.01.

EXAMPLE 52

N-(3,5-Dinitrobenzoyl)-N-(2-ethoxy-2-oxoethyl)glycine ethyl ester

A solution of 5.0 g (21.7 mmol) of 3,5-dinitrobenzoyl chloride in 75 ml of methylene chloride was added dropwise with stirring to an ice bath cooled mixture of 4.7 ml (27 mmol) of diethyl iminodiacetate and 6.0 ml (43 mmol) of triethylamine in 25 ml of methylene chloride. The reaction mixture was stirred in the cooling bath for 30 minutes and then was left at room temperature for 21 hours. After washing with NaHCO₃ solution, the organic layer was dried and concentrated to an oil which was chromatographed on 150 g of silica gel using 20–30% ethyl acetate-hexane. The combined pure fractions were recrystallized from methanol to give 5.95 g (72% yield, 79°–80°) of N-(3,5-dinitrobenzoyl)-N-(2-ethoxy-2-oxoethyl)glycine ethyl ester. The nmr and mass spectra were consistent with the structure.

EXAMPLE 53

N-(3,5-Diaminobenzoyl)-N-(2-ethoxy-2-oxoethyl)glycine ethyl ester

A mixture of 5.95 g of N-(3,5-dinitrobenzoyl)-N-(2-ethoxy-2-oxoethyl)glycine ethyl ester and 0.75 g of 10% palladium on carbon in 75 ml of THF was shaken under an initial hydrogen pressure of 54 psi in a Parr Hydrogenator until uptake ceased after 2.5 hours. The catalyst was removed by filtration and the filtrate was concentrated at reduced pressure to give 4.9 g of N-(3,5-diaminobenzoyl)-N-(2-ethoxy-2-oxoethyl)glycine ethyl ester as a yellow oil. The mass spectrum was compatible with the structure.

EXAMPLE 54

N-(2-Ethoxy-2-oxoethyl)-N-[3,5-bis(1-oxotetradecylamino)benzoyl]glycine ethyl ester A solution of 1.9 ml (7 mmol) of myristoyl chloride in 10 ml of anhydrous THF was added dropwise to a stirred, ice cooled mixture of 1.0 g (3.09 mmol) of N-(3,5-diaminobenzoyl)-N-(2-ethoxy-2-oxoethyl)glycine ethyl ester and 1.7 ml (12.4 mmol) of triethylamine in 20 ml of anhydrous THF. The reaction mixture was stirred in the cooling bath for 30 minutes and then at room temperature for 24 hours. The solvent was removed at reduced pressure and the residue was extracted with ethyl acetate. After washing with NaHCO₃ solution, the dried extract was concentrated to an oil which was purified by chromatography on 120 g of silica gel using 40% ethyl acetate-hexane to give 2.1 g (91% yield) of N-(2-ethoxy-2-oxoethyl)-N-[3,5-bis(1-oxotetradecylamino)benzoyl]glycine ethyl ester as a yellow oil. The nmr and mass spectra were consistent with the structure.

EXAMPLE 55

N-(2-Ethoxy-2-oxoethyl)-N-[3,5-bis(1-oxohexadecylamino)benzoyl]glycine ethyl ester The reaction of palmitoyl chloride with N-(3,5-diaminobenzoyl)-N-(2-ethoxy-2-oxoethyl)glycine ethyl ester as in Example 54 gave N-(2-ethoxy-2-oxoethyl)-N-[3,5-bis(1-oxohexadecylamino)benzoyl]glycine ethyl ester as an oil after chromatography on silica gel using 35% ethyl acetate-hexane.

EXAMPLE 56

N-(Carboxymethyl)-N-[3,5-bis(1-oxotetradecylamino)-benzoyl]glycine

A solution of 2.1 g (2.8 mmol) of N-(2-ethoxy-2-oxoethyl)-N-[3,5-bis(1-oxotetradecylamino)benzoyl]glycine ethyl ester and 2.35 ml (14 mmol) of 6N NaOH in 75 ml of methanol was stirred at reflux for 5 hours under an argon atmosphere. The solvent was removed at reduced pressure and the residue was acidified. The product was extracted with ethyl acetate and the dried extract was concentrated to a solid which was recrystallized from acetonitrile to give 1.54 g (79% yield, mp 109°-111°) of N-(carboxymethyl)-N-[3,5-bis(1-oxotetradecylamino)-benzoyl]glycine.

Anal. Calcd for $C_{39}H_{65}N_3O_7 \cdot 1.3\ H_2O$: C, 65.85, H, 9.58; N, 5.91; $H_2O$, 3.30. Found: C, 66.08; H, 9.50; N, 5.81; $H_2O$, 3.63.

EXAMPLE 57

N-(Carboxymethyl)-N-[3,5-bis(1-oxohexadecylamino)benzoyl]glycine

Sodium hydroxide hydrolysis of N-(2-ethoxy-2-oxoethyl)-N-[3,5-bis(1-oxohexadecylamino)benzoyl]glycine ethyl ester as in Example 56 and recrystallization from methanol-water gave N-(carboxymethyl)-N-[3,5-bis(1-oxohexadecylamino)benzoyl]glycine, mp 129°-133°.

Anal. Calcd for $C_{43}H_{73}N_3O_7 \cdot 1.5\ H_2O$: C, 66.98; H, 9.93; N, 5.44; $H_2O$, 3.50. Found: C, 67.29; H, 9.80; N, 5.44; $H_2O$, 4.29.

EXAMPLE 58

2-Hydroxy-5-(octadecyloxy)benzoic acid methyl ester

A mixture of 2.0 g (11.9 mmol) of 2,5-dihydroxybenzoic acid methyl ester, 4.55 g (13.1 mmol) of 1-bromooctadecane and 1.9 g (13.7 mmol) of potassium carbonate in 50 ml of acetone was stirred at reflux for 24 hours. The solvent was removed at reduced pressure and the residue was treated with water. The product was extracted with ethyl acetate and the dried extract was concentrated to a solid which was recrystallized from ethyl acetate-hexane to give 3.5 g (70% yield, mp 53°-54°) of 2-hydroxy-5-(octadecyloxy)benzoic acid methyl ester.

Anal. Calcd for $C_{26}H_{44}O_4$: C, 74.24; H, 10.54. Found: C, 74.45; H, 10.89.

EXAMPLE 59

5-(Octadecyloxy)-2-(phenylmethoxy)benzoic acid methyl ester

A mixture of 2.5 g (5.95 mmol) of 2-hydroxy-5-(octadecyloxy)benzoic acid methyl ester, 0.78 ml (6.54 mmol) of benzyl bromide and 4.1 g (29.8 mmol) of potassium carbonate in 100 ml of acetone and 10 ml of DMF was stirred at reflux under an argon atmosphere for 24 hours. The solvent was removed at reduced pressure and the residue was treated with water. The product was extracted with ethyl ether and the dried extract was concentrated to a solid which was purified by HPLC using 5% ethyl acetate-hexane to give 2.5 g (82% yield, mp 52°-54°) of 5-(octadecyloxy)-2-(phenylmethoxy)benzoic acid methyl ester.

Anal. Calcd for $C_{33}H_{50}O_4$: C, 77.60; H, 9.87. Found: C, 77.81; H, 10.03.

EXAMPLE 60

5-(Octadecyloxy)-2-(phenylmethoxy)benzoic acid

A suspension of 2.4 g (4.7 mmol) of 5-(octadecyloxy)-2-(phenylmethoxy)benzoic acid methyl ester in 70 ml of methanol and 23 ml (23 mmol) of 1.0N NaOH was stirred at reflux for 4 hours when a clear solution was obtained. The solvent was removed at reduced pressure and the residue was treated with water, acidified to pH 1 with 3N HCl and the product was extracted with chloroform. The dried extract was concentrated to a solid which was recrystallized from ether-hexane to give 2.33 g (99% yield, mp 80°-81°) of 5-(octadecyloxy)-2-(phenylmethoxy)benzoic acid.

Anal. Calcd for $C_{32}H_{48}O_4$: C, 77.38; H, 9.74. Found: C, 77.43; H, 9.73.

EXAMPLE 61

N-[5-(Octadecyloxy)-2-(phenylmethoxy)benzoyl]-N-[2-(phenylmethoxy)-2-oxoethyl]glycine phenylmethyl ester A mixture of 1.0 g (2.0 mmol) of 5-(octadecyloxy)-2-(phenylmethoxy)benzoic acid in 5 ml of thionyl chloride was heated to reflux for 1 hour and then concentrated at reduced pressure. The resultant acid chloride was dissolved in 30 ml of anhydrous THF and added dropwise to a stirred mixture of 0.785 g (2.5 mmol) of dibenzyl iminodiacetate and 0.85 ml (6.1 mmol) of triethylamine in 10 ml of THF. The reaction mixture was stirred at room temperature for 20 hours and the solvent was removed at reduced pressure. The product was purified by HPLC using 5% ethyl acetate-hexane to give 0.70 g (44% yield) of N-[5-(octadecyloxy)-2-(phenylmethoxy) benzoyl]-N-[2-(phenylmethoxy)-2-oxoethyl]glycine phenylmethyl ester as an oil.

Anal. Calcd for $C_{50}H_{65}NO_7$: C, 75.82; H, 8.27; N, 1.77. Found: C, 75.92; H, 8.40; N, 1.74.

EXAMPLE 62

N-(Carboxymethyl)-N-[2-hydroxy-5-(octadecyloxy)benzoyl]glycine

A mixture of 0.60 g of N-[5-(octadecyloxy)-2-(phenylmethoxy) benzoyl]-N-[2-(phenylmethoxy)-2-oxoethyl]glycine phenylmethyl ester and 0.20 g of 10% palladium on carbon in 20 ml of THF was stirred under a hydrogen atmosphere at room temperature for 23 hours. The catalyst was removed by filtration and the filtrate was concentrated at reduced pressure to a solid which was triturated with ether to give 0.27 g (68% yield, mp 128°-132°) of N-(carboxymethyl)-N-[2-hydroxy-5-(octadecyloxy)benzoyl]glycine.

Anal. Calcd for $C_{29}H_{47}NO_7$: C, 66.77; H, 9.08; N, 2.68. Found: C, 66.47; H, 9.24; N, 2.64.

EXAMPLE 63

4-(Octadecyloxy)-alpha-oxobenzeneacetic acid

To 0.325 g (8.1 mmol) of a 60% oil dispersion of NaH suspended in 15 ml of anhydrous DMF and stirred under an argon atmosphere at room temperature was added 1.5 g (7.73 mmol) of 4-hydroxyalpha-oxobenzeneacetic acid ethyl ester. The reaction mixture was stirred at room temperature for 20 minutes and a solution of 3.2 g (9.66 mmol) of 1-bromooctadecane in 20 ml of anhydrous DMF was added dropwise over 15 minutes. After stirring at reflux for 16 hours, 5 ml of acetic acid was added and the solvent was removed at reduced pressure. Water was added to the residue and the product was extracted with methylene chloride. The dried extract was concentrated at reduced pressure and the solid residue was purified by HPLC using 50% methylene chloride-hexane to give 2.9 g (84% yield, mp 46°–48°) of 4-(octadecyloxy)-alpha-oxobenzeneacetic acid ethyl ester.

Anal. Calcd for $C_{28}H_{46}O_4$: C, 75.29; H, 10.38. Found: C, 75.48; H, 10.35.

To 2.9 g (6.45 mmol) of 4-(octadecyloxy)-alpha-oxobenzeneacetic acid ethyl ester in 200 ml of hot methanol was added 7.1 ml (7.1 mmol) of 1.0 N NaOH. The reaction mixture was stirred at reflux for 5 minutes, 50 ml of water was added and the solvents were removed at reduced pressure. Water (300 ml) was added and the product was extracted with methylene chloride-THF (4:1). The dried extract was concentrated at reduced pressure and the residual solid was recrystallized from acetone-hexane to give 2.39 g (88% yield, mp 78°–80°) of 4-(octadecyloxy)-alpha-oxobenzeneacetic acid.

Anal. Calcd for $C_{26}H_{42}O_4$: C, 74.60; H, 10.11. Found: C, 74.56: H, 10.24.

EXAMPLE 64

N-(2-Ethoxy-2-oxoethyl)-N-[2-[4-(octadecyloxy)-phenyl]-1,2-dioxoethyl]glycine ethyl ester To a suspension of 1.99 g (4.75 mmol) of 4-(octadecyloxy)-alpha-oxobenzeneacetic acid in 100 ml of methylene chloride and 3 drops of DMF stirred and cooled in an ice bath was added 2.1 ml (23.8 mmol) of oxalyl chloride. After 5 minutes the ice bath was removed and stirring was continued at room temperature for 1 hour. The reaction mixture was concentrated at reduced pressure and the resultant acid chloride was dissolved in 75 ml of anhydrous methylene chloride and added dropwise to an ice cooled solution of 1.25 ml (7.1 mmol) of diethyl iminodiacetate and 1.3 ml (9.5 mmol) of triethylamine in 25 ml of methylene chloride. The reaction mixture was stirred at room temperature for 17 hours and washed with $NaHCO_3$ solution, dried and concentrated at reduced pressure. The resultant solid was recrystallized from methanol to give 2.4 g (86% yield, mp 63°–64°) of N-(2-ethoxy-2-oxoethyl)-N-[2-[4-(octadecyloxy)phenyl]-1,2-dioxoethyl]glycine ethyl ester.

Anal. Calcd for $C_{34}H_{55}NO_7$: C, 69.24; H, 9.40; N, 2.37. Found: C, 68.72; H, 9.31; N, 2.26.

EXAMPLE 65

N-(Carboxymethyl)-N-[2-[4-(octadecyloxy)phenyl]-1,2-dioxoethyl]glycine

A mixture of 0.7 g (1.19 mmol) of N-(2-ethoxy-2-oxoethyl)-N-[2-[4-(octadecyloxy)phenyl]-1,2-dioxoethyl]glycine ethyl ester and 1.0 ml (6.0 mmol) of 6.0 N NaOH in 75 ml of methanol was stirred at reflux under an argon atmosphere for 4 hours. After removal of the solvent at reduced pressure, the residue was acidified with dilute HCl and the product was extracted with ethyl acetate. The dried extract was concentrated at reduced pressure to a solid which was recrystallized from acetone-hexane to give 0.6 g (95% yield, mp 130°–132°) of N-(carboxymethyl)-N-[2-[4-(octadecyloxy)phenyl]-1,2-dioxoethyl]glycine.

Anal. Calcd for $C_{30}H_{47}NO_7$: C, 67.51; H, 8.88; N, 2.66. Found: C, 67.45; H, 8.80: N, 2.54.

EXAMPLE 66

3-(Octadecyloxy)-alpha-oxobenzeneacetic acid methyl ester

A mixture of 2.0 g (14.7 mmol) of 3-hydroxyacetophenone, 5.9 g (17.6 mmol) of 1-bromooctadecane and 4.1 g (29.4 mmol) of anhydrous potassium carbonate in 35 ml of anhydrous DMF was stirred and heated at 80° for 45 hours. The solvent was removed under high vacuum, the residue was treated with 50 ml of 0.5 N HCl and the resultant solid was filtered and recrystallized from methanol to give 3.35 g (59% yield, mp 50°–52°) of 3-octadecyloxyacetophenone.

A mixture of 3.3 g (8.5 mmol) of 3-octadecyloxyacetophenone and 1.89 g (17 mmol) of selenium dioxide in 35 ml of pyridine was stirred and heated at 100° under argon for 24 hours. The reaction mixture was filtered through a Celite pad which was washed with 40 ml of methylene chloride. The filtrate was cooled in an ice bath and stirred during the dropwise addition of 4.6 ml (60 mmol) of methyl chloroformate. The ice bath was removed and stirring was continued at room temperature for 15 minutes. Methylene chloride (50 ml) was added, the solution was washed with 3N HCl and with $NaHCO_3$ solution, dried and concentrated at reduced pressure to a solid. Purification by HPLC using 40% ethyl acetate-hexane followed by recrystallization from methylene chloride-methanol gave 3.0 g (82% yield, mp 50°–52°) of 3-(octadecyloxy)-alpha-oxobenzeneacetic acid methyl ester.

Anal. Calcd for $C_{27}H_{44}O_4$: C, 74.96; H, 10.25. Found: C, 75.12; H, 10.05.

EXAMPLE 67

3-(Octadecyloxy)-alpha-oxobenzeneacetic acid

To 2.98 g (6.9 mmol) of 3-(octadecyloxy)-alpha-oxobenzeneacetic acid methyl ester in 200 ml of hot methanol was added 7.6 ml (7.6 mmol) of 1N NaOH. The solution was stirred at reflux for 5 minutes and the solvent was then removed under reduced pressure. The residue was treated with water and 15 ml of 1N HCl and the product was extracted with ethyl acetate. The dried extract was concentrated to a solid which was recrystallized form acetone-hexane to give 2.5 g (88% yield, mp 77°–79°) of 3-(octadecyloxy)-alpha-oxobenzeneacetic acid.

Anal. Calcd for $C_{26}H_{42}O_4$: C, 74.60; H, 10.11. Found: C, 74.69; H, 10.29.

EXAMPLE 68

N-(2-Ethoxy-2-oxoethyl)-N-[2-[3-(octadecyloxy)-phenyl]-1,2-dioxoethyl]glycine ethyl ester To a solution of 1.0 g (2.4 mmol) of 3-(octadecyloxy)-alpha-oxobenzeneacetic acid in 50 ml of anhydrous methylene chloride and 2 drops of DMF stirred in an ice bath was added 1.1 ml (11.9 mmol) of oxalyl chloride. The cooling bath was removed and stirring was continued at room temperature for 2 hours. The solvent was removed at reduced pressure and the residual acid chloride was dissolved in 40 ml of anhydrous methylene chloride and added dropwise to a stirred, ice bath cooled solution of 0.6 ml (3.6 mmol) of diethyl iminodiacetate and 0.66 ml (4.8 mmol) of triethylamine in 10 ml of methylene chloride. The mixture was stirred for 30 minutes in the ice bath and then at room temperature for 19 hours when it was washed with $NaHCO_3$ solution, dried and concentrated to an oil which was purified by chromatography on 35 g of 230-400 mesh silica gel using 20% ethyl acetate-hexane to give 1.3 g (93% yield, mp 27°-29°) of N-(2-ethoxy-2-oxoethyl)-N-[2-[3-(octadecyloxy)phenyl]-1,2-dioxoethyl]glycine ethyl ester.

Anal. Calcd for $C_{34}H_{55}NO_7$: C, 69.24; H, 9.40; N, 2.37. Found: C, 69.24; H, 9.36; N, 2.40.

EXAMPLE 69

N-(Carboxymethyl)-N-[2-[3-(octadecyloxy)phenyl]-1,2-dioxoethyl]glycine

A solution of 1.3 g (2.2 mmol) of N-(2-ethoxy-2-oxoethyl)-N-[2-[3-(octadecyloxy)phenyl]-1,2-dioxoethyl]glycine ethyl ester and 1.8 ml (11 mmol) of 6N NaOH in 100 ml of methanol was stirred at reflux under argon for 3 hours. The solvent was removed at reduced pressure, the residue was acidified and the product was extracted with ethyl acetate. The dried extract was concentrated at reduced pressure to a solid which was recrystallized from acetone-hexane to give 1.08 g (91% yield, mp 126°-128°) of N-(carboxymethyl)-N-[2-[3-(octadecyloxy)phenyl]-1,2-dioxoethyl]glycine.

Anal. Calcd for $C_{30}H_{47}NO_7$: C, 67.51; H, 8.88; N, 2.62. Found: C, 67.47; H, 8.67; N, 2.60.

EXAMPLE 70

3,5-bis(Decyloxy)-alpha-oxobenzeneacetic acid methyl ester

A mixture of 2.0 g (13 mmol) of 3,5-dihydroxyacetophenone, 8.7 ml (42 mmol) of 1-bromodecane and 7.3 g (53 mmol) of anhydrous potassium carbonate in 35 ml of anhydrous DMF was stirred and heated at 80° for 66 hours under argon. The solvent was removed at reduced pressure, 50 ml of 0.5N HCl was added to the residue and the product was filtered and recrystallized from methanol to give 4.2 g (73% yield, mp 50°-52°) of 3,5-bis(decyloxy)acetophenone. The nmr and mass spectra were consistent with the structure.

A mixture of 4.15 g (9.6 mmol) of 3,5-bis(decyloxy)acetophenone and 2.13 g (19.2 mmol) of selenium dioxide in 40 ml of pyridine was stirred and heated at 100° under argon for 24 hours. The reaction mixture was filtered through a Celite pad which was washed with 80 ml of methylene chloride. The filtrate was cooled and stirred in an ice bath during the dropwise addition of 5.6 ml (73 mmol) of methyl chloroformate. The ice bath was removed and stirring was continued at room temperature for 15 minutes. The mixture was washed with 3N HCl, with NaHCO$_3$ solution, dried and concentrated to a solid which was purified by HPLC using 40% ethyl acetate-hexane followed by recrystallization from methylene chloride-methanol to give 2.74 g (60% yield, mp 49°-50°) of 3,5-bis(decyloxy)-alpha-oxobenzeneacetic acid methyl ester.

Anal. Calcd for $C_{29}H_{48}O_5$: C, 73.07; H, 10.15. Found: C, 72.91; H, 9.99.

EXAMPLE 71

3,5-bis(Decyloxy)-alpha-oxobenzeneacetic acid

To 2.7 g (5.7 mmol) of 3,5-bis(decyloxy)-alpha-oxobenzeneacetic acid methyl ester in 400 ml of hot methanol was added 6.2 ml (6.2 mmol) of 1.0N NaOH and the solution was stirred at reflux for 5 minutes. The solvent was removed at reduced pressure, water and 10 ml of 1N HCl were added to the residue and the product was extracted with ethyl acetate. The dried extract was concentrated to give 2.55 g (97% yield) of 3,5-bis(decyloxy)-alpha-oxobenzeneacetic acid as a waxy solid.

Anal. Calcd for $C_{28}H_{46}O_5$: C, 72.69; H, 10.02. Found: C, 72.52; H, 9.72.

EXAMPLE 72

N-[[3,5-bis(Decyloxy)phenyl]-1,2-dioxoethyl]-N-(2-ethoxy-2-oxoethyl)glycine ethyl ester To a solution of 1.0 g (2.16 mmol) of 3,5-bis(decyloxy)-alpha-oxobenzeneacetic acid in 50 ml of anhydrous methylene chloride and 2 drops of DMF stirred in an ice bath was added 0.94 ml (10.8 mmol) of oxalyl chloride. The cooling bath was removed and stirring was continued at room temperature for 2 hours. The solvent was removed at reduced pressure and the residual acid chloride was dissolved in 40 ml of anhydrous methylene chloride and added dropwise to an ice bath cooled solution of 0.6 ml (3.2 mmol) of diethyl iminodiacetate and 0.6 ml (4.3 mmol) of triethylamine in 10 ml of methylene chloride. After stirring in the ice bath for 30 minutes and at room temperature for 18 hours, the reaction mixture was washed with NaHCO$_3$, dried and concentrated at reduced pressure to an oil which was purified by chromatography on 25 g of 230-400 mesh silica gel using 20% ethyl acetate-hexane to give 1.2 g (91% yield) of N-[[3,5-bis(decyloxy)phenyl]-1,2-dioxoethyl]-N-(2-ethoxy-2-oxoethyl)glycine ethyl ester as an oil. The nmr and mass spectra served to confirm the structure.

EXAMPLE 73

N-(Carboxymethyl)-N-[[3,5-bis(decyloxy)phenyl]-1,2-dioxoethyl]glycine

A solution of 1.2 g (1.9 mmol) of N-[[3,5-bis(decyloxy)phenyl]-1,2-dioxoethyl]-N-(2-ethoxy-2-oxoethyl)glycine ethyl ester in 75 ml of methanol and 1.6 ml (9.6 mmol) of 6.0 N NaOH was stirred at reflux under argon for 4 hours. The solvent was removed at reduced pressure, the residue was treated with water and 2.5 ml of 6N HCl and the product was extracted with ethyl acetate. The dried extract was concentrated to a foam which was crystallized from hexane to give 0.96 g (87% yield, mp 76°-78°) of N-(carboxymethyl)-N-[[3,5-bis(decyloxy)phenyl]-1,2-dioxoethyl]glycine.

Anal. Calcd for $C_{32}H_{51}NO_8$: C, 66.52; H, 8.90; N, 2.42. Found: C, 66.44; H, 8.77; N, 2.23.

EXAMPLE 74

N-[3-(Octadecyloxy)benzoyl]glycine

A solution of 1.0 g (2.56 mmol) of 3-(octadecyloxy)benzoic acid in 20 ml of thionyl choride was refluxed for 2 hours and was then concentrated at reduced pressure to give the acid chloride. This was dissolved in 20 ml of anhydrous THF and added dropwise to an ice bath cooled suspension of 0.36 g (2.8 mmol) of glycine methyl ester hydrochloride and 1.1 ml (7.68 mmol) of triethylamine in 10 ml of methylene chloride. The reaction mixture was stirred at room temperature for 20 hours and then was concentrated at reduced pressure to a solid. Water was added and the solid was filtered to give 1.1 g, mp 69°-70°, of N-[3-(octadecyloxybenzoyl]glycine methyl ester.

Anal. Calcd for $C_{28}H_{47}NO_4$: C, 72.84; H, 10.26; N, 3.03. Found: C, 72.50; H, 10.12; N, 3.34.

A solution of 1.1 g (2.4 mmol) of N-[3-(octadecyloxybenzoyl] glycine methyl ester and 1.3 ml (7.8 mmol) of 6N NaOH in 50 ml of methanol was stirred at reflux for 18 hours. The solvent was removed at reduced pressure, the residue was acidified and the product was extracted with ethyl acetate. The dried extract was concentrated to a solid which was recrystallized from methanol-water to give 0.53 g, mp 100°–109°, of N-[3-(octadecyloxy)-benzoyl] glycine.

Anal. Calcd for $C_{27}H_{45}NO_4$: C, 72.44; H, 10.13, N, 3.13. Found: C, 72.02; H, 10.05; N, 3.06.

EXAMPLE 75

3-(Octadecyloxy)phenylacetic acid

A mixture of 1.0 g (6 mmol) of 3-hydroxyphenylacetic acid methyl ester, 2.2 g (6.6 mmol) of 1-bromooctadecane and 3.7 g (27 mmol) of anhydrous potassium carbonate in 80 ml of anhydrous acetone and 15 ml of DMF was stirred at reflux for 67 hours. The solvent was removed at reduced pressure, water was added to the residue and the product was extracted with ethyl acetate. The dried extract was concentrated to a solid which was purified by chromatography on 150 g of silica gel using 10% ethyl acetate-hexane to give 2.0 g (80% yield, mp 43°–45°) of 3-(octadecyloxy) phenylacetic acid methyl ester. The mass and nmr spectra were consistent with the structure.

A solution of 2.0 g (4.78 mmol) of 3-(octadecyloxy)-phenylacetic acid methyl ester and 3.0 ml (18 mmol) of 6N NaOH in 30 ml of dioxane and 75 ml of methanol was stirred at reflux for 17 hours. The solvents were removed at reduced pressure and the residue was acidified and filtered to give 1.8 g, mp 69°–73°, of 3-(octadecyloxy) phenylacetic acid. The nmr and mass spectra were consistent with the structure.

EXAMPLE 76

N-(Carboxymethyl)-N-[3-(octadecyloxy)-phenylacetyl]glycine

A solution of 1.9 g (4.78 mmol) of 3-(octadecyloxy)-phenylacetic acid in 40 ml of thionyl chloride was refluxed for 1.5 hours. The excess thionyl chloride was removed at reduced pressure and the resultant acid chloride was dissolved in 40 ml of anhydrous methylene chloride. This solution was added dropwise to an ice bath cooled mixture of 1.0 g (6 mmol) of dimethyl iminodiacetate and 1.4 ml (10 mmol) of triethylamine in 25 ml of methylene chloride. The reaction mixture was kept at room temperature for 17 hours and then was washed with 1N HCl, dried and concentrated to a solid. Purification by chromatography on 150 g of silica gel using 40% ethyl acetate-hexane gave 1.7 g (65% yield, mp 52°–55°) of N-(2-methoxy-2-oxoethyl)-N-[3-(octadecyloxy)phenylacetyl]glycine methyl ester.

Anal. Calcd for $C_{32}H_{53}NO_6$: C, 70.17; H, 9.75; N, 2.56. Found: C, 70.36; H, 9.72; N, 2.62.

A solution of 1.7 g (3.1 mmol) of N-(2-methoxy-2-oxoethyl)-N-[3-(octadecyloxy)phenylacetyl]glycine methyl ester and 2.6 ml (15.6 mmol) of 6N NaOH in 50 ml of dioxane and 100 ml of methanol was stirred at reflux for 17 hours. After cooling to room temperature, the solid was filtered and shaken with excess 1N HCl to liberate the acid from its sodium salt. The solid was filtered and dried under high vacuum over $P_2O_5$ to give 0.84 g, mp 90°–93°, of N-(carboxymethyl)-N-[3-(octadecyloxy)phenylacetyl]glycine.

Anal. Calcd for $C_{30}H_{49}NO_6$: C, 69.33; H, 9.50; N, 2.70. Found: C, 69.60; H, 9.36; N, 2.63.

EXAMPLE 77

(E)-3-[(3-Octadecyloxy)phenyl]-2-propenoic acid

A mixture of 1 g (5.2 mmol) of (E)-3-hydroxyphenylpropenoic acid ethyl ester, 1.9 g (5.7 mmol) of 1-bromooctadecane and 3.2 g (23.2 mmol) of anhydrous potassium carbonate in 50 ml of acetone and 15 ml of DMF was stirred at reflux for 41 hours. The solvents were removed at reduced pressure, water was added to the residue and the product was filtered and recrystallized from ethanol-water to give 1.98 g (86% yield, mp 43°–44°) of (E)-3-[(3-octadecyloxy) phenyl]-2-propenoic acid ethyl ester.

Anal. Calcd for $C_{29}H_{48}O_3$: C, 78.33, H, 10.88. Found: C, 78.28; H, 10.88.

A solution of 1.39 g (3.1 mmol) of (E)-3-[(3-octadecyloxy)phenyl]-2-propenoic acid ethyl ester and 1.6 ml (9.6 mmol) of 6N NaOH in 50 ml of ethanol was stirred at reflux for 1 hour. Water and 1N HCl were added to the reaction mixture and the product was extracted with hot ethyl acetate. The extract was concentrated to a solid which was recystallized from ethanol-water to give 1.12 g, mp 97°–98°, of (E)-3-[(3-octadecyloxy)phenyl]-2-propenoic acid.

Anal. Calcd for $C_{27}H_{44}O_3$: C, 77.84; H, 10.64. Found: C, 77.60; H, 10.64.

EXAMPLE 78

(E)-N-(Carboxymethyl)-N-[3-[(3-octadecyloxy)-phenyl]-1-oxo-2-propenyl]glycine To a stirred, ice bath cooled suspension of 1.0 g (2.4 mmol) of (E)-3-[(3-octadecyloxy)phenyl]-2-propenoic acid suspended in 50 ml of anhydrous methylene chloride and 2 drops of DMF was added 0.63 ml (7.2 mmol) of oxalyl chloride. The reaction mixture was stirred at room temperature for one hour and the solvent was removed at reduced pressure. The acid chloride was dissolved in 75 ml of methylene chloride and added dropwise to an ice bath cooled, stirred solution of 0.53 ml of diethyl iminodiacetate and 0.7 ml of triethylamine in 10 ml of methylene chloride. The reaction mixture was stirred at room temperature for 17 hours and then was washed with NaHCO3 solution, dried and concentrated to a solid which was recrystallized from ether-methanol to give 1.17 g (83% yield, mp 62°–63°) of (E)-N-(2-ethoxy-2-oxoethyl)-N-[3-[(3-octadecyloxy)phenyl]-1-oxo-2-propenyl]glycine ethyl ester. The nmr and mass spectra were consistent with the structure.

A solution of 1.17 g (1.99 mmol) of (E)-N-(2-ethoxy-2-oxoethyl)-N-[3-[(3-octadecyloxy)phenyl]-1-oxo-2-propenyl]glycine ethyl ester and 1.3 ml (7.8 mmol) of 6N NaOH in 75 ml of methanol was stirred at reflux for 5 hours. After cooling to room temperature, the solid was removed by filtration, acidified with 6N HCl and the product was extracted with ethyl acetate. The dried extract was concentrated to a solid which was recrystallized from acetone-hexane to give 0.89 g, mp 173°–175°, of (E)-N-(carboxymethyl)-N-[3-[(3-octadecyloxy)-phenyl]-1-oxo-2-propenyl]glycine.

Anal. Calcd for $C_{31}H_{49}NO_6$: C, 70.02; H, 9.29; N, 2.63. Found: C, 70.01; H, 9.38; N, 2.36.

EXAMPLE 79

N-(Carboxymethyl)-N-[3-[(3-octadecyloxy)phenyl]-1-oxopropyl]glycine

A mixture of 0.40 g of (E)-N-(carboxymethyl)-N-[3-[(3-octadecyloxy)phenyl]-1-oxo-2-propenyl]glycine and 0.1 g of 10% palladium on carbon in 25 ml of THF was stirred in a hydrogen atmosphere at room temperature for 2 hours. The catalyst was removed by filtration and the filtrate was concentrated at reduced pressure to a solid which was triturated with hexane and filtered to give 0.34 g, mp 112°-115°, of N-(carboxymethyl)-N-[3-[(3-octadecyloxy)phenyl]-1-oxopropyl]glycine.

Anal. Calcd for $C_{31}H_{51}NO_6$: C, 69.76, H, 9.63; N, 2.62. Found: C, 69.66; H, 9.80; N, 2.58.

EXAMPLE 80

N-(2-Ethoxy-2-oxoethyl)-N-[5-(octadecyloxy)-2-(phenylmethoxy)benzoyl]glycine ethyl ester A solution of 5.6 g (11.3 mmol) of 5-(octadecyloxy)-2-(phenylmethoxy)benzoic acid in 36 ml of thionyl chloride and 9 ml of anhydrous pyridine was stirred at reflux for 1 hour. The reaction mixture was concentrated to dryness at reduced pressure. Anhydrous toluene was added to the residue and the solution was concentrated again at reduced pressure to give the solid acid chloride. This was suspended in 240 ml of anhydrous THF and stirred at room temperature while 2.8 g (14.7 mmol) of diethyl iminodiacetate in 25 ml of methylene chloride and 5 ml (35.8 mmol) of triethyl-amine were added. The reaction mixture was stirred at room temperature for 25 hours and the solvents were removed at reduced pressure. The residue was extracted with ethyl acetate, the extract was washed with water, dried and concentrated to an oil. Purification by HPLC using 20% ethyl acetate-hexane gave 6.6 g (88% yield, mp 61°-62°) of N-(2-ethoxy-2-oxoethyl)-N-[5-(octadecyloxy)-2-(phenylmethoxy)benzoyl]glycine ethyl ester. The nmr and mass spectra were compatible with the structure.

EXAMPLE 81

N-(Carboxymethyl)-N-[5-(octadecyloxy)-2-(phenylmethoxy)benzoyl]glycine

A mixture of 6.6 g (9.9 mmol) of N-(2-ethoxy-2-oxoethyl)-N-[5-(octadecyloxy)-2-(phenylmethoxy)benzoyl]glycine ethyl ester and 25 ml (50 mmol) of 2N NaOH in 300 ml of methanol was stirred at reflux for 2 hours. The solvent was removed at reduced pressure, the residue was acidified and the product was extracted with ethyl acetate. The dried extract was concentrated to an oil which was treated with water and cooled in the refrigerator. The resultant solid was filtered, triturated with ether-hexane and filtered again to give 5.8 g (96% yield, mp 81°-83°) of N-(carboxymethyl)-N-[5-(octadecyloxy)-2-(phenylmethoxy)benzoyl]glycine.

Anal. Calcd for $C_{36}H_{53}NO_7$: C, 70.67; H, 8.73; N, 2.29. Found: C, 70.36; H, 9.00; N, 2.19.

EXAMPLE 82

2-(Hydroxy-5-(tetradecyloxy)benzoic acid methyl ester

The reaction of 2,5-dihydroxybenzoic acid methyl ester with 1-bromotetradecane under conditions described in Example 58 gave 2-(hydroxy-5-(tetradecyloxy)benzoic acid methyl ester (43% yield, mp 49°-53°). The nmr and mass spectra were compatible with the structure.

EXAMPLE 83

2-(Phenylmethoxy)-5-(tetradecyloxy)benzoic acid methyl ester

The reaction of 2-(hydroxy-5-(tetradecyloxy)benzoic acid methyl ester with benzyl bromide under conditions described in Example 59 gave 2-(phenylmethoxy)-5-(tetradecyloxy)benzoic acid methyl ester (82% yield, mp 43°-46°).

EXAMPLE 84

2-(Phenylmethoxy)-5-(tetradecyloxy)benzoic acid

Sodium hydroxide hydrolysis of 2-(phenylmethoxy)-5-(tetradecyloxy)benzoic acid methyl ester under conditions described in Example 60 gave 2-(phenylmethoxy)-5-(tetradecyloxy)benzoic acid (94% yield, mp 73°-74°).

Anal. Calcd for $C_{28}H_{40}O_4$: C, 76.33; H, 9.15. Found: C, 76.00; H, 9.13.

EXAMPLE 85

N-(2-Ethoxy-2-oxoethyl)-N-[5-(tetradecyloxy)-2-(phenylmethoxy)benzoyl]glycine ethyl ester The reaction of 2-(phenylmethoxy)-5-(tetradecyloxy)benzoic acid chloride with diethyl iminodiacetate under conditions described in Example 80 gave N-(2-ethoxy-2-oxoethyl)-N-[5-(tetradecyloxy)-2-(phenylmethoxy)benzoyl]glycine ethyl ester (82% yield, mp 49°-50°).

EXAMPLE 86

N-(Carboxymethyl)-N-[5-(tetradecyloxy)-2-(phenylmethoxy)benzoyl]glycine

Sodium hydroxide hydrolysis of N-(2-ethoxy-2-oxoethyl)-N-[5-(tetradecyloxy)-2-(phenylmethoxy)benzoyl]glycine ethyl ester under conditions described in Example 81 gave N-(carboxymethyl)-N-[5-(tetradecyloxy)-2-(phenylmethoxy)benzoyl]glycine (91% yield, mp 71°-74°).

Anal. Calcd for $C_{32}H_{45}NO_7$: C, 69.16; H, 8.16; N, 2.52. Found: C, 69.20; H, 8.18; N, 2.28.

EXAMPLE 87

5-(Decyloxy)-2-hydroxybenzoic acid methyl ester

The reaction of 2,5-dihydroxybenzoic acid methyl ester with 1-bromodecane under conditions described in Example 58 gave 5-(decyloxy)-2-hydroxybenzoic acid methyl ester (51% yield, mp 40°-43°).

EXAMPLE 88

5-(Decyloxy)-2-(phenylmethoxy)benzoic acid methyl ester

The reaction of 5-(decyloxy)-2-hydroxybenzoic acid methyl ester with benzyl bromide under conditions described in Example 59 gave 5-(decyloxy)-2-(phenylmethoxy)benzoic acid methyl ester (81% yield, mp 32°-34°).

EXAMPLE 89

5-(Decyloxy)-2-(phenylmethoxy)benzoic acid

Sodium hydroxide hydrolysis of 5-(decyloxy)-2-(phenylmethoxy) benzoic acid methyl ester under conditions described in Example 60 gave 5-(decyloxy)-2-(phenylmethoxy)benzoic acid (88% yield, mp 63°-65°).

Anal. Calcd for $C_{24}H_{32}O_4$: C, 74.97; H, 8.39. Found: C, 74.86; H, 8.51.

EXAMPLE 90

N-(2-Ethoxy-2-oxoethyl)-N-[5-(decyloxy)-2-(phenylmethoxy)benzoyl]glycine ethyl ester The reaction of 5-(decyloxy)-2-(phenylmethoxy)benzoic acid chloride with diethyl iminodiacetate under conditions described in Example 80 gave N-(2-ethoxy-2-oxoethyl)-N-[5-(decyloxy)-2-(phenylmethoxy)benzoyl]glycine ethyl ester (82% yield, mp 37°–38°).

EXAMPLE 91

N-(Carboxymethyl)-N-[5-(decyloxy)-2-(phenylmethoxy)benzoyl]glycine

Sodium hydroxide hydrolysis of N-(2-ethoxy-2-oxoethyl)-N-[5-(decyloxy)-2-(phenylmethoxy)benzoyl]glycine ethyl ester under conditions described in Example 81 gave N-(carboxymethyl)-N-[5-(decyloxy)-2-(phenylmethoxy)benzoyl]glycine (94% yield, mp 74°–78°).

Anal. Calcd for $C_{28}H_{37}NO_7$: C, 67.32; H, 7.46; N, 2.80. Found: C, 67.23; H, 7.47; N, 2.70.

EXAMPLE 92

5-(Octadecyloxy)-2-(3-phenylpropoxy)benzoic acid methyl ester

A mixture of 0.60 g (1.43 mmol) of 2-hydroxy-5-(octadecyloxy) benzoic acid methyl ester, 0.25 ml (1.6 mmol) of 3-bromopropylbenzene and 1 g (7.2 mmol) of potassium carbonate in 20 ml of anhydrous acetone and 2 ml of DMF was stirred at reflux for 24 hours. An additional 0.06 ml of 3-bromopropylbenzene was added and reflux was continued for 18 hours. The solvents were removed at reduced pressure and the residue was extracted with ethyl acetate. The dried extract was concentrated to an oil which was crystallized from methanol-hexane to give 0.60 g (78% yield, mp 46°–48°) of 5-(octa-decyloxy)-2-(3-phenylpropoxy)benzoic acid methyl ester.

EXAMPLE 93

5-(Octadecyloxy)-2-(3-phenylpropoxy)benzoic acid

Sodium hydroxide hydrolysis of 5-(octadecyloxy)-2-(3-phenylpropoxy)benzoic acid methyl ester under conditions described in Example 60 gave 5-(octadecyloxy)-2-(3-phenylpropoxy)benzoic acid (84% yield, mp 68°–70°).

Anal. Calcd for $C_{34}H_{52}O_4$: C, 77.82; H, 9.99. Found: C, 77.66; H, 10.03.

EXAMPLE 94

N-(2-Ethoxy-2-oxoethyl)-N-[5-(octadecyloxy)-2-(3-phenylpropoxy)benzoyl]glycine ethyl ester The reaction of 5-(octadecyloxy)-2-(3-phenylpropoxy)benzoic acid chloride with diethyl iminodiacetate under conditions described in Example 80 gave N-(2-ethoxy-2-oxoethyl)-N-[5-(octadecyloxy)-2-(3-phenylpropoxy)benzoyl]glycine ethyl ester (92% yield, mp 54°–55°).

EXAMPLE 95

N-(Carboxymethyl)-N-[5-(octadecyloxy)-2-(3-phenylpropoxy)benzoyl]glycine

Sodium hydroxide hydrolysis of N-(2-ethoxy-2-oxoethyl)-N-[5-(octadecyloxy)-2-(3-phenylpropoxy)benzoyl]glycine ethyl ester under conditions described in Example 81 gave N-(carboxymethyl)-N-[5-(octadecyloxy)-2-(3-phenylpropoxy)benzoyl]glycine 82% yield, mp 101°–102°).

Anal. Calcd for $C_{38}H_{57}NO_7$: C, 71.33; H, 8.98; N, 2.19. Found: C, 71.47; H, 9.07; N, 2.11.

EXAMPLE 96

5-(Octadecyloxy)-2-[3-[4-(phenylmethoxy)phenoxy]propoxy]benzoic acid methyl ester The reaction of 2-hydroxy-5-(octadecyloxy)benzoic acid methyl ester with 3-[(4-phenylmethoxy)phenoxy]propyl bromide under conditions described in Example 92 gave 5-(octadecyloxy)-2-[3-[4-(phenylmethoxy)phenoxy]propoxy]benzoic acid methyl ester (74% yield, mp 79°–81°).

EXAMPLE 97

5-(Octadecyloxy)-2-[3-[4(phenylmethoxy)phenoxy]propoxy]benzoic acid

Sodium hydroxide hydrolysis of 5-(octadecyloxy)-2-[3-[4-(phenylmethoxy)phenoxy]propoxy]benzoic acid methyl ester under conditions described in Example 60 gave 5-(octadecyloxy)-2-[3-[4-(phenylmethoxy)phenoxy]propoxy]benzoic acid (88% yield, mp 92°–95°).

EXAMPLE 98

N-(2-Ethoxy-2-oxoethyl)-N-[5-(octadecyloxy)-2-[3-[4-(phenylmethoxy)phenoxy]propoxy]benzoyl]glycine ethyl ester The reaction of 5-(octadecyloxy)-2-[3-[4-phenylmethoxy)phenoxy]propoxy]benzoic acid chloride with diethyl iminodiacetate under conditions described in Example 80 gave N-(2-ethoxy-2-oxoethyl)-N-[5-(octadecyloxy)-2-[3-[4-(phenylmethoxy)phenoxy]propoxy]benzoyl]glycine ethyl ester (92% yield, mp 54°–55°).

EXAMPLE 99

N-(Carboxymethyl)-N-[5-(octadecyloxy)-2-[3-[4-(phenylmethoxy)phenoxy]propoxy]benzoyl]glycine Sodium hydroxide hydrolysis of N-(2-ethoxy-2-oxoethyl)-N-[5-(octadecyloxy)-2-[3-[4-(phenylmethoxy)phenoxy]propoxy]benzoyl] glycine ethyl ester under conditions described in Example 81 gave N-(carboxymethyl)-N-[5-(octadecyloxy)-2-[3-[4-(phenylmethoxy)phenoxy]propoxy]benzoyl]glycine (79% yield, mp 70°–74° ).

Anal. Calcd for $C_{45}H_{63}NO_9$: C, 70.92; H, 8.33; N, 1.84. Found: C, 70.61; H, 8.30; N, 1.75.

EXAMPLE 100

N-(Carboxymethyl)-N-[2-[3-(4-hydroxyphenoxy)propoxy]-5-(octadecyloxy)phenyl]benzoyl]glycine Catalytic hydrogenolysis of N-(carboxymethyl)-N-[5-(octadecyloxy)-2-[3-[4-(phenylmethoxy)phenoxy]propoxy]benzoyl]glycine under conditions described in Example 62 gave N-(carboxymethyl)-N-[2-[3-(4-hydroxyphenoxy)propoxy]-5-(octadecyloxy)phenyl]benzoyl]glycine (76% yield, mp 110°–114°). Anal. Calcd for $C_{38}H_{57}NO_9$: C, 67.93; H, 8.55; N, 2.08. Found: C, 67.64; H, 8.57; N, 1.98.

EXAMPLE 101

5-[[6-([1,1'-Biphenyl]-4-yloxy)hexyl]oxy]-2-hydroxybenzoic acid methyl ester

A mixture of 1.0 g (6 mmol) of 2,5-dihydroxybenzoic acid methyl ester, 2.0 g (6 mmol) of 6-([1,1'-biphenyl]-4-yloxy)hexyl bromide and 1.24 g (9 mmol) of potassium carbonate in 50 ml of acetone and 5 ml of DMF was stirred at reflux for 27 hours. The solvents were removed at reduced pressure, water was added to the residue and the product was extracted with ethyl acetate. The dried extract was concentrated to a solid which was purified by chromatography on 40 g of silica gel using 50% toluene-hexane to give 1.4 g (56% yield, mp 91°–92°) of 5-[[6-([1,1'-biphenyl]4-yloxy)hexyl]oxy]-2-hydroxybenzoic acid methyl ester. The structure was confirmed by nmr and mass spectra.

EXAMPLE 102

5-[[6-([1,1'-Biphenyl]-4-yloxy)hexyl]oxy]-2-(phenylmethoxy)benzoic acid methyl ester A mixture of 1.4 g (3.3 mmol) of 5-[[6-([1,1'-biphenyl]-4-yloxy) hexyl]oxy]-2-hydroxybenzoic acid methyl ester, 0.6 ml (5 mmol) of benzyl bromide and 2.5 g (16.5 mmol) of potassium carbonate in 50 ml of acetone and 5 ml of DMF was stirred at reflux for 24 hours. After the usual workup, the crude product was recrystallized from ethyl acetate-hexane to give 1.5 g (89% yield, mp 85°–87°) of 5-[[6-([1,1'-biphenyl]-4-yloxy)hexyl]oxy]-2-(phenylmethoxy)benzoic acid methyl ester.

EXAMPLE 103

5-[[6-([1,1'-Biphenyl]-4-yloxy)hexyl]oxy]-2-(phenylmethoxy)benzoic acid

Sodium hydroxide hydrolysis of 5-[[6-([1,1'-biphenyl]-4-yloxy)hexyl]oxy]-2-(phenylmethoxy)benzoic acid methyl ester as described in Example 60 gave 5-[[6-([1,1'-biphenyl]-4-yloxy)hexyl]oxy]-2-(phenylmethoxy)benzoic acid (96% yield, mp 131°–133°).

EXAMPLE 104

N-(2-Ethoxy-2-oxoethyl)-N-[5-[[6-([1,1'-biphenyl]-4-yloxy)hexyl]oxy]-2-(phenylmethoxy)benzoyl]glycine ethyl ester The reaction of 5-[[6-([1,1'-biphenyl]-4-yloxy)hexyl]oxy]-2-(phenylmethoxy)benzoic acid chloride with diethyl iminodiacetate under conditions described in Example 80 gave, after purification by HPLC using 25% ethyl acetate-hexane, N-(2-ethoxy-2-oxoethyl)-N-[5-[[6-([1,1'-biphenyl]-4-yloxy)hexyl]oxy]-2-(phenylmethoxy) benzoyl]glycine ethyl ester (74% yield, mp 60°–62°). The structure was confirmed by nmr and mass spectra.

EXAMPLE 105

N-[5-[[6-([1,1'-biphenyl]-4-yloxy)hexyl]oxy]-2-(phenylmethoxy)benzoyl]-N-(carboxymethyl)glycine Sodium hydroxide hydrolysis of N-(2-ethoxy-2-oxoethyl)-N-[5-[[6-([1,1'-biphenyl]-4-yloxy)hexyl]oxy]-2-(phenylmethoxy)benzoyl]glycine ethyl ester under conditions described in Example 81 gave N-[5-[[6-([1,1'-biphenyl]-4-yloxy)hexyl]oxy]-2(phenylmethoxy)benzoyl]-N-(carboxymethyl)glycine (82% yield, mp 98°–100°).

Anal. Calcd for $C_{36}H_{37}NO_8$: C, 70.69; H, 6.10; N, 2.29. Found: C, 70.49; H, 5.66; N, 2.30.

EXAMPLE 106

2-Hydroxy-5-[(12-phenoxydodecyl)oxy]benzoic acid methyl ester

The reaction of 2,5-dihydroxybenzoic acid methyl ester with 12-phenoxydodecyl bromide under condition described in Example 101 gave 2-hydroxy-5-[(12-phenoxydodecyl)oxy]benzoic acid methyl ester (75% yield, mp 61°–64°).

EXAMPLE 107

5-[(12-Phenoxydodecyl)oxy]-2-(phenylmethoxy)benzoic acid methyl ester

The reaction of 2-hydroxy-5-[(12-phenoxydodecyl)oxy]benzoic acid methyl ester with benzyl bromide as described in Example 102 gave 5-[(12-phenoxydodecyl)oxy]-2-(phenylmethoxy) benzoic acid methyl ester (58% yield, mp 46°–48°).

EXAMPLE 108

5-[(12-Phenoxydodecyl)oxy]-2-(phenylmethoxy)benzoic acid

Sodium hydroxide hydrolysis of 5-[(12-phenoxydodecyl)oxy]-2-(phenylmethoxy)benzoic acid methyl ester using conditions described in Example 60 gave 5-[(12-phenoxydodecyl)oxy]-2-(phenylmethoxy)benzoic acid (94% yield, mp 85°–87°).

EXAMPLE 109

N-(2-Ethoxy-2-oxoethyl)-N-[5-[(12-phenoxydodecyl)oxy]-2-(phenylmethoxy)benzoyl]glycine ethyl ester The reaction of 5-[(12-phenoxydodecyl)oxy]-2-(phenylmethoxy) benzoic acid chloride with diethyl iminodiacetate under conditions described in Example 80 gave N-(2-ethoxy-2-oxoethyl)-N-[5-[(12-phenoxydodecyl)oxy]-2-(phenylmethoxy)benzoyl]glycine ethyl ester (56% yield, mp 49°–50°). The structure was confirmed by nmr and mass spectra.

EXAMPLE 110

N-(Carboxymethyl)-N-[5-[(12-phenoxydodecyl)oxy]-2-(phenylmethoxy)benzoyl]glycine Sodium hydroxide hydrolysis of N-(2-ethoxy-2-oxoethyl)-N-[5-[(12-phenoxydodecyl)oxy]-2-(phenylmethoxy)benzoyl]glycine ethyl ester using conditions described in Example 81 gave N-(carboxymethyl)-N-[5-[(12-phenoxydodecyl)oxy]-2-(phenylmethoxy)benzoyl]glycine (65% yield, mp 70°–75°).

EXAMPLE 111 alpha-Oxo-4-[(12-phenoxydodecyl)oxy]benzeneacetic acid ethyl ester

To a suspension of 0.162 g (4.06 mmol) of 60% sodium hydride on oil in 10 ml of anhydrous DMF was added 0.75 g (3.87 mmol) of 4-hydroxy-alpha-oxobenzeneacetic acid ethyl ester. The reaction mixture was stirred at room temperature under argon for 15 minutes and then 1.4 g (4.06 mmol) of 12-phenoxydodecyl bromide in 20 ml of anhydrous DMF was added. The mixture was stirred and heated at 60° for 24 hours. The usual workup followed by chromatography on 45 g of silica gel gave alpha-oxo-4-[(12-phenoxydodecyl)oxy]-benzeneacetic acid ethyl ester (83% yield, mp 58°–59°).

EXAMPLE 112 alpha-Oxo-4-[(12-phenoxydodecyl)oxy]benzeneacetic acid

To 1.44 g (3.17 mmol) of alpha-oxo-4-[(12-phenoxydodecyl)oxy]benzeneacetic acid ethyl ester in 100 ml of hot methanol was added 3.5 ml (3.5 mmol) of 1N NaOH. The mixture was heated on a steam bath for 5 minutes, water (20 ml) was added and the solvents were removed at reduced pressure. Water (100 ml) and 7.0 ml of 1.0N HCl were added to the residue and the product was extracted with methylene chloride-THF (4:1). The dried extract was concentrated at reduced pressure to a solid which was recrystallized from acetone-hexane to give 1.14 g (84% yield, mp 98°–100°) of alpha-oxo-4-[(12-phenoxydodecyl)oxy]benzeneacetic acid Anal. Calcd for $C_{26}H_{34}O_5$: C, 73.21; H, 8.03. Found: C, 73.13; H, 8.03.

EXAMPLE 113

N-(2-Ethoxy-2-oxoethyl)-N-[1,2-dioxo-2-[4-[(12-phenoxydodecyl)oxy]phenyl]ethyl]glycine ethyl ester To 1.12 g (2.6 mmol) of alpha-oxo-4-[(12-phenoxydodecyl)oxy]benzeneacetic acid in 50 ml of methylene chloride containing 2 drops of anhydrous DMF stirred and cooled in an ice bath was added 1.1 ml (13 mmol) of oxalyl chloride. The cooling bath was removed and stirring was continued at room temperature for 1.5 hours. The solvent was removed at reduced pressure and the resultant solid acid chloride was dissolved in 50 ml of methylene chloride and added dropwise to a stirred, ice bath cooled solution of 0.7 ml (5.25 mmol) of diethyl iminodiacetate and 0.7 ml (5.25 mmol) of triethylamine in 15 ml of methylene chloride. The reaction mixture was stirred at room temperature for 16 hours and then was concentrated at reduced pressure. The resultant crude product was triturated with methanol and filtered to give 1.32 g (84% yield, mp 55°–56°) of N-(2-ethoxy-2-oxoethyl)-N-[1,2-dioxo-2-[4-[(12-phenoxydodecyl)oxy]phenyl]ethyl]glycine ethyl ester. The nmr and mass spectra were consistent with the structure.

EXAMPLE 114

N-(Carboxymethyl)-N-[1,2-dioxo-2-[4-[(12-phenoxydodecyl)oxy]phenyl]ethyl]glycine A mixture of 1.3 g (2.17 mmol) of N-(2-ethoxy-2-oxoethyl)-N-[1,2-dioxo-2-[4-[(12-phenoxydodecyl)oxy]phenyl]ethyl]glycine ethyl ester and 1.8 ml (10.8 mmol) of 6N NaOH in 125 ml of methanol was stirred at reflux for 3.5 hours. The reaction mixture was cooled in an ice bath and the precipitated sodium salt was filtered. The sodium salt was suspended in water, acidified with 6N HCl and extracted with ethyl acetate. The dried extract was concentrated to a solid which was triturated with hexane and filtered to give 1.04 g (88% yield, mp 130°–132°) of N-(carboxymethyl)-N-[1,2-dioxo-2-[4-[(12-phenoxydodecyl)oxy]phenyl]ethyl]glycine.

Anal. Calcd for $C_{30}H_{39}NO_8$: C, 66.53; H, 7.26; N, 2.59. Found: C, 66.45; H, 7.44; N, 2.47.

EXAMPLE 115

TABLET FORMULATION (Wet Granulation)

| Item | Ingredients | 5 mg | 10 mg | 25 mg | 100 mg | 250 mg | 500 mg |
|---|---|---|---|---|---|---|---|
| 1. | Compound A* | 5 | 10 | 25 | 100 | 250.0 | 500 |
| 2. | Lactose Anhydrous DTG | 125 | 120 | 105 | 30 | 75.0 | 150 |
| 3. | Pregelatinized Starch | 6 | 6 | 6 | 6 | 15.0 | 30 |
| 4. | Microcrystalline Cellulose | 30 | 30 | 30 | 30 | 75.0 | 150 |
| 5. | Magnesium Stearate | 1 | 1 | 1 | 1 | 2.5 | 5 |
|  | Total | 167 | 167 | 167 | 167 | 417.5 | 835 |

*N-(carboxymethyl)-N-[2-[4-(octadecyloxy)phenyl]-1,2-dioxoethyl]glycine

Manufacture Procedure:
1. Mix Items 1, 2, 3 and 4 and granulate with water.
2. Dry the granulation at 50° C. overnight.
3. Pass the granulation through suitable milling equipment.
4. Add Item 5 and mix for three minutes; compress on a suitable press.

EXAMPLE 116

CAPSULE FORMULATION

| Item | Ingredients | 5 mg | 10 mg | 25 mg | 100 mg | 250 mg | 500 mg |
|---|---|---|---|---|---|---|---|
| 1. | Compound A* | 5 | 10 | 25 | 100 | 250.0 | 500 |
| 2. | Corn Starch | 103 | 98 | 83 | 8 | 20.0 | 403.3 |
| 3. | Modified Starch | 4 | 4 | 4 | 4 | 10.0 | 20 |
| 4. | Talc | 4 | 4 | 4 | 4 | 10.0 | 20 |
| 5. | Magnesium Stearate | 1 | 1 | 1 | 1 | 2.5 | 5 |
|  | Total | 117 | 117 | 117 | 117 | 292.5 | 585 |

Manufacture Procedure:
1. Mix Items 1, 2, and 3 and granulate with water.
2. Dry the granulation at 50° C. overnight.
3. Mill through a suitable screen using appropriate milling equipment.
4. Add Items 4 and 5 and mix for five minutes.

EXAMPLE 117

| o/w Cream, 5% | |
|---|---|
| Ingredients | % by Wt. |
| Compound B* | 5.0 |
| Petrolatum (and) Lanolin (and) Lanolin Alcohol | 5.0 |
| Isodecyl Oleate | 1.0 |
| Octyl Palmitate | 1.0 |
| Disopropyl Adipate | 1.0 |
| Cetearyl Alcohol (and) Ceteareth 20 (Promulgen D) | 5.0 |
| Cetyl Alcohol | 1.0 |
| Stearyl Alcohol | 1.0 |
| Steareth —10 (Brij 76) | 1.0 |
| Steareth —20 (Brij 78) | 1.0 |
| Purified Water | 74.0 |
| Preservatives | q.s. |

*N-(carboxymethyl)-N-[5-(octadecyloxy)-2-(phenylmethoxy)benzoyl]glycine

1. Heat the petrolatum, lanolin, and lanolin alcohol mixture isodecyl oleate, octyl palmitate, diisopropyl adipate, cetearyl alcohol and ceteareth 20 mixture, cetyl alcohol, stearyl alcohol, steareth —10 and steareth 20 to 70°–80° C. Mix until all components have melted and are dissolved.
2. Heat the purified water to 70°–80° C. Add water soluble preservatives to the heated water and mix until dissolved.
3. Add the oil soluble preservatives to the lipid phase (Step 1). Mix until dissolved.
4. Dissolve the drug in the lipid phase from Step 3. Mix vigorously until the drug is dissolved.
5. Add Step 2 to Step 4. Homogenize until a uniform emulsion is formed.
6. Continue stirring the emulsion and cool to room temperature.

EXAMPLE 118

| Hydrophilic Ointment 5% | |
|---|---|
| Ingredients | % by Wt. |
| Compound B* | 5.0 |
| Petrolatum (and) Lanolin Alcohol (Amerchol CAB) | 10.0 |
| Isopropyl Lanolate (Amerlate P) | 5.0 |
| Petrolatum | 25.0 |
| Cetyl Alcohol | 2.0 |
| Stearyl Alcohol | 2.0 |
| Steareth —10 (Brij —76) | 2.0 |
| Steareth —20 (Brij —78) | 2.0 |
| Methyl Gluceth —20 (Glucam E-20) | 5.0 |
| Purified Water | 42.0 |
| Preservatives | q.s. |

1. Heat the petrolatum, and lanolin alcohol mixture, isopropyl lanolate, petrolatum, cetyl alcohol, stearyl alcohol, steareth —10 and steareth —20 to 70°, 80° C. Mix until all components have melted and are dissolved.
2. Heat the purified water to 70°-80° C. Add water soluble preservatives to the heated water and mix until dissolved.
3. Add oil soluble preservatives to the lipid phase of Step 1. Mix until dissolved.
4. Dissolve the drug in the lipid phase from Step 3. Mix vigorously until the drug is dissolved.
5. Add Step 2 to Step 4. Homogenize until a uniform consistency is obtained.
6. Continue stirring the emulsion and cool to room temperature.

EXAMPLE 119

| Ointment (Anhydrous) 5.0% | |
|---|---|
| Ingredients | % by Wt. |
| Compound B* | 5.0 |
| White Petrolatum | 38.0 |
| Mineral Oil, 70 vis. | 10.0 |
| Sorbitan Sesquioleate (Arlacel 83) | 5.0 |
| Petrolatum (and) Lanolin Alcohol (Amerchol CAB) | 15.0 |
| Isopropyl Lanolate (Amerlate P) | 6.0 |
| Mineral Oil (and) Lanolin Alcohol (Amerchol L101) | 10.0 |
| Acetylated Lanolin (Modulan) | 10.0 |
| Paraffin Wax | 2.0 |
| Preservatives | q.s. |

1. Heat white petrolatum, mineral oil, sorbitan sesquioleate, petrolatum and lanolin alcohol mixture, isopropyl lanolate, mineral oil and lanolin alcohol mixture, acetylated lanolin and parafin was to 70°-80° C. Mix until all components have melted and are dissolved.
2. Cool the mixture from Step 1 to 50° C. and add the preservatives. Mix until dissolved.
3. Add the drug to Step 2. Mix vigorously until drug is dissolved.
4. Cool Step 3 to room temperature with stirring.

We claim:

1. A compound of the formula

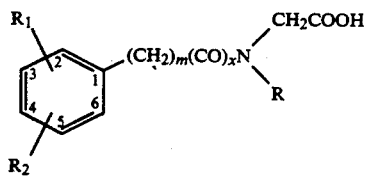

R is —CH$_2$COOH;
m is 0–2,
x is 1–2, with the provision that when x is 2, m is always 0;
R$_1$ is CH$_3$(CH$_2$)$_n$O—, CH$_3$(CH$_2$)$_n$CONH—, CH$_3$(CH$_2$)$_n$NHCONH—, CH$_3$(CH$_2$)$_n$NHCOO—, HOOC(CH$_2$)$_p$O— or R$_3$(CH$_2$)$_q$O—;

R$_2$ is hydrogen, carboxy, hydroxy, nitro, amino, CH$_3$(CH$_2$)$_n$O—, CH$_3$(CH$_2$)$_n$CONH—, CH$_3$(CH$_2$)$_n$NHCONH—, CH$_3$(CH$_2$)$_n$NHCOO—, HOOC(CH$_2$)$_p$O—, R$_3$(CH$_2$)$_q$O— or R$_4$[O(CH$_2$)$_2$]$_r$O—, wherein n is 0–17, p is 1–10, q is 1–12, r is 1–6, R$_3$ is 1- or 2-naphthyloxy, 2,3- or 3,4-dihydroxyphenyl, phenyl, phenoxy or substituted phenyl or phenoxy, wherein the substituent is selected from the group consisting of lower alkyl, lower alkoxy, hydroxy, nitro, amino, halo, carboxy or phenyl, and R$_4$ is lower alkyl;

or a pharmaceutically acceptable salt thereof with a base.

2. A compound, in accordance with claim 1, wherein the substitution pattern is

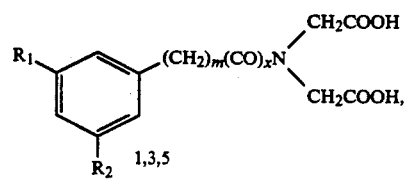

1,3,5

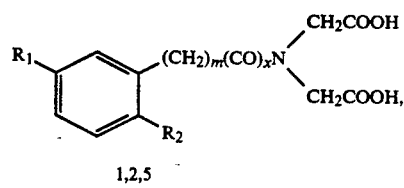

1,2,5

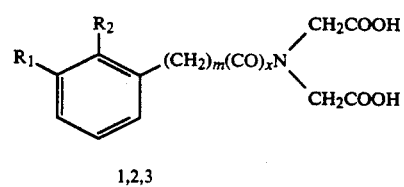

1,2,3 or

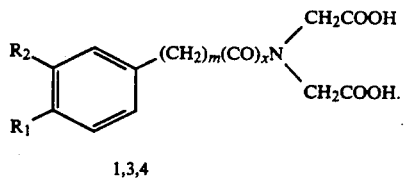

1,3,4

3. A compound, in accordance with claim 1, wherein the substitution pattern is 1,3,5; R is —CH$_2$COOH; m is 0; x is 1–2; R$_1$ and R$_2$ are the same and are CH$_3$(CH$_2$)$_n$O—, CH$_3$(CH$_2$)$_n$CONH— or HOOC(CH$_2$)$_p$O, wherein n is 3–17 and p is 5–10.

4. A compound, in accordance with claim 1, wherein the substitution pattern is 1,3,5 or 1,2,5; R is —CH$_2$COOH; m is 0; x is 1–2; R$_1$ is CH$_3$(CH$_2$)$_n$O—, wherein n is 3–17, or R$_3$(CH$_2$)$_q$O—; R$_2$ is hydrogen, hydroxyl, nitro, amino, R$_3$(CH$_2$)$_q$O—, R$_4$[O(CH$_2$)$_2$]$_r$O, or HOOC(CH$_2$)$_p$O—.

5. A compound, in accordance with claim 1, wherein the substitution pattern is 1,3,5; R is —CH$_2$COOH; m is 0; x is 1–2; R$_1$ and R$_2$ are the same and are CH$_3$(CH$_2$)$_n$O— or CH$_3$(CH$_2$)$_n$CONH—, wherein n is 9–17.

6. A compound, in accordance with claim 1, wherein the substitution pattern is 1,3,5 or 1,2,5; R is —CH- 2COOH; m is 0; x is 1-2; $R_1$ is $CH_3(CH_2)_nO$— wherein n is 9-17, or $R_3(CH_2)_qO$—, wherein $R_3$ is phenoxy or phenyl substituted phenoxy, q is 6-12; and $R_2$ is hydrogen, hydroxy or $R_3(CH_2)_qO$—, wherein $R_3$ is phenyl or phenoxy substituted by benzyloxy or hydroxy, and q is 1-3.

7. A compound, in accordance with claim 1, N-(carboxymethyl)-N-[3-(octadecyloxy)benzoyl]glycine.

8. A compound in accordance with claim 1, N-(carboxymethyl)-N-[[3,5-bis(decyloxy)phenyl]carbonyl]glycine.

9. A compound in accordance with claim 1, N-(carboxymethyl)-N-[3-[2-[2-(2-ethoxyethoxy)ethoxy]ethoxy]-5(-octadecyloxy)benzoyl]glycine.

10. A compound in accordance with claim 1, N-(carboxymethyl)-N-[3,5-bis(1-oxotetradecylamino)benzoyl]glycine.

11. A compound in accordance with claim 1, N-(carboxymethyl)-N-[2-hydroxy-5-(octadecyloxy)benzoyl]glycine.

12. A compound in accordance with claim 1, N-(carboxymethyl)-N-[2-[4-(octadecyloxy)phenyl]-1,2-dioxoethyl]glycine.

13. A compound in accordance with claim 1, N-(carboxymethyl)-N-[5-(octadecyloxy)-2-(phenylmethoxy)benzoyl]glycine.

14. A pharmaceutical composition comprising a compound of the formula

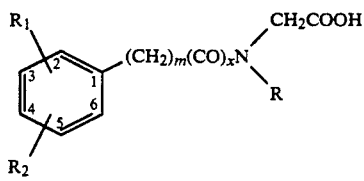

R is —$CH_2COOH$;

m is 0-2, x is 1-2, with the provision that when x is 2, m is always 0;

$R_1$ is $CH_3(CH_2)_nO$—, $CH_3(CH_2)_nCONH$—, $CH_3(CH_2)_nNHCONH$—, $CH_3(CH_2)_nNHCOO$—, $HOOC(CH_2)_pO$— or $R_3(CH_2)_qO$—;

$R_2$ is hydrogen, carboxy, hydroxy, nitro, amino, $CH_3(CH_2)_nO$—, $CH_3(CH_2)_nCONH$—, $CH_3(CH_2)_nNHCONH$—, $CH_3(CH_2)_nNHCOO$—, $HOOC(CH_2)_pO$—, $R_3(CH_2)_qO$— or $R_4[O(CH_2)_2]_rO$—, wherein n is 0-17, p is 1-10, q is 1-12, r is 1-6, $R_3$ is 1- or 2- naphthyloxy, 2,3- or 3,4-dihydroxyphenyl, phenyl, phenoxy or substituted phenyl or phenoxy, wherein the substituent is selected from the group consisting of lower alkyl, lower alkoxy, hydroxy, nitro, amino, halo, carboxy or phenyl, and $R_4$ is lower alkyl;

or a pharmaceutically acceptable salt thereof with a base, and an inert carrier.

15. A pharmaceutical composition, in accordance with claim 14, wherein the compound of formula 1 has the substitution pattern:

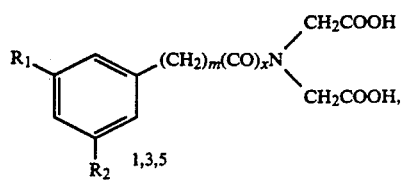

1,3,5

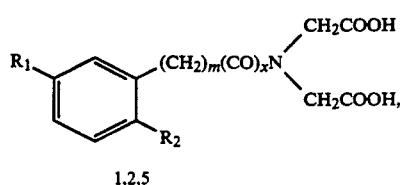

1,2,5

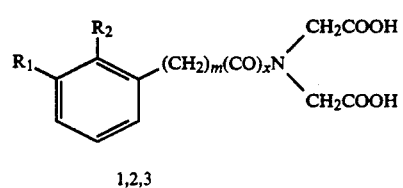

1,2,3 or

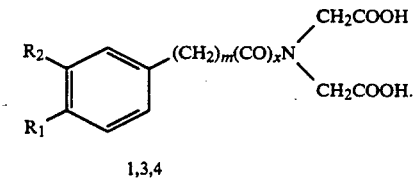

1,3,4

16. A pharmaceutical composition, in accordance with claim 14, wherein the compound of formula 1 has the substitution pattern 1,3,5; R is —$CH_2COOH$; m is 0; x is 1-2; $R_1$ and $R_2$ are the same and are $CH_3(CH_2)_nO$—, $CH_3(CH_2)_nCONH$—, or $HOOC(CH_2)_pO$, wherein n is 3-17 and p is 5-10.

17. A pharmaceutical composition, in accordance with claim 14, wherein the substitution pattern is 1,3,5 or 1,2,5; R is —$CH_2COOH$; m is 0; x is 1-2; $R_1$ is $CH_3(CH_2)_nO$—, wherein n is 3-17, or $R_3(CH_2)_qO$—; $R_2$ is hydrogen, hydroxyl, nitro, amino, $R_3(CH_2)_qO$—, $R_4[O(CH_2)_2]_rO$, or $HOOC(CH_2)_pO$—.

18. A pharmaceutical composition, in accordance with claim 14, wherein the substitution pattern is 1,3,5; R is —$CH_2COOH$; m is 0; x is 1-2; $R_1$ and $R_2$ are the same and are $CH_3(CH_2)_nO$—or $CH_3(CH_2)_nCONH$—, wherein n is 9-17.

19. A pharmaceutical composition, in accordance with claim 14, wherein the substitution pattern is 1,3,5 or 1,2,5; R is —$CH_2COOH$; m is 0; x is 1-2; $R_1$ is $CH_3(CH_2)_nO$—, wherein n is 9-17, or $R_3(CH_2)_qO$—, wherein $R_3$ is phenoxy or phenyl substituted phenoxy, q is 6-12; and $R_2$ is hydrogen, hydroxy or $R_3(CH_2)_qO$— wherein $R_3$ is phenyl or phenoxy substituted by benzyloxy or hydroxy, and q is 1-3.

* * * * *